US011029296B2

(12) United States Patent
Garcia et al.

(10) Patent No.: US 11,029,296 B2
(45) Date of Patent: Jun. 8, 2021

(54) SYSTEM AND METHOD FOR MONITORING A REFORMING CATALYST

(71) Applicant: Chevron Phillips Chemical Company LP, The Woodlands, TX (US)

(72) Inventors: Israel Garcia, Kingwood, TX (US); Scott G. Morrison, Kingwood, TX (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 32 days.

(21) Appl. No.: 16/549,090

(22) Filed: Aug. 23, 2019

(65) Prior Publication Data
US 2019/0376941 A1 Dec. 12, 2019

Related U.S. Application Data

(63) Continuation of application No. 15/805,948, filed on Nov. 7, 2017, now Pat. No. 10,436,762.

(51) Int. Cl.
*F01N 11/00* (2006.01)
*G01N 33/00* (2006.01)
*C10G 69/00* (2006.01)
*G01N 30/00* (2006.01)
(Continued)

(52) U.S. Cl.
CPC ......... *G01N 33/0047* (2013.01); *C10G 69/00* (2013.01); *G01N 30/00* (2013.01); *G01N 30/88* (2013.01); *G01N 33/005* (2013.01); *G01N 33/0063* (2013.01); *G01N 33/0067* (2013.01); *G06T 11/206* (2013.01); *C10G 2300/4031* (2013.01); *C10G 2400/30* (2013.01); *G01N 2030/0095* (2013.01); *G01N 2033/0068* (2013.01)

(58) Field of Classification Search
CPC ...... F01N 11/00; G01M 15/10; G01M 15/102
USPC ....................................... 73/114.75
See application file for complete search history.

(56) References Cited

U.S. PATENT DOCUMENTS

| | | | |
|---|---|---|---|
| 2,773,014 A | 12/1956 | Snuggs et al. | |
| 2,863,822 A | 12/1958 | Sage | |
| 2,880,161 A | 3/1959 | Moore et al. | |

(Continued)

FOREIGN PATENT DOCUMENTS

| | | |
|---|---|---|
| CN | 101824337 A | 9/2010 |
| EP | 0007219 A1 | 1/1980 |

(Continued)

OTHER PUBLICATIONS

Foreign communication from a related counterpart application—International Search Report and Writen Opinion, PCT/US2012/056306, dated Nov. 29, 2012, 8 pages.

(Continued)

*Primary Examiner* — Eric S. McCall
(74) *Attorney, Agent, or Firm* — Conley Rose, P.C.

(57) ABSTRACT

A method of monitoring catalytic performance of a catalyst used in a reforming process, comprising a) collecting gaseous component data from the reforming process; b) calculating a gaseous component ratio from the gaseous component data; and c) utilizing the gaseous component ratio to estimate an amount of catalytic activity remaining in the catalyst used in the reforming process, a number of days on stream remaining for the catalyst used in the reforming process, or both.

10 Claims, 8 Drawing Sheets

(51) Int. Cl.
    *G06T 11/20* (2006.01)
    *G01N 30/88* (2006.01)

(56) References Cited

U.S. PATENT DOCUMENTS

| | | | |
|---|---|---|---|
| 2,883,337 A | 4/1959 | Hartley et al. | |
| 2,944,000 A | 7/1960 | Ginter | |
| 3,154,481 A | 10/1964 | Brooks | |
| 3,733,476 A | 5/1973 | Hopkins et al. | |
| 3,806,447 A | 4/1974 | Hayes et al. | |
| 3,974,064 A | 8/1976 | Bajek et al. | |
| 4,028,430 A | 6/1977 | Stine et al. | |
| 4,072,729 A | 2/1978 | Stine et al. | |
| 4,125,454 A | 11/1978 | Clem et al. | |
| 4,166,024 A | 8/1979 | Swan | |
| 4,191,633 A | 3/1980 | Dauber | |
| 4,208,397 A | 6/1980 | Coates | |
| 4,348,271 A | 9/1982 | Swan | |
| 4,384,948 A | 5/1983 | Barger | |
| 4,415,435 A | 11/1983 | Lewis | |
| 4,425,222 A | 1/1984 | Swan | |
| 4,810,683 A | 3/1989 | Cohn et al. | |
| 4,830,732 A | 5/1989 | Mohr et al. | |
| 4,851,380 A | 7/1989 | Van Leirsburg et al. | |
| 4,855,269 A | 8/1989 | Mohr | |
| 4,882,040 A | 11/1989 | Dessau et al. | |
| 4,925,819 A | 5/1990 | Fung et al. | |
| 4,937,215 A | 6/1990 | Murakawa et al. | |
| 4,954,245 A | 9/1990 | Miller et al. | |
| 5,066,628 A | 11/1991 | Miller et al. | |
| 5,106,798 A | 4/1992 | Fung | |
| 5,155,075 A | 10/1992 | Innes et al. | |
| RE34,250 E | 5/1993 | Van Leirsburg et al. | |
| 5,260,238 A | 11/1993 | Murakawa et al. | |
| 5,391,292 A | 2/1995 | Schortheide et al. | |
| 5,401,386 A | 3/1995 | Morrison et al. | |
| 5,520,798 A | 5/1996 | Innes | |
| 5,601,698 A | 2/1997 | Innes | |
| 5,676,821 A | 10/1997 | Heyse et al. | |
| 5,776,849 A | 7/1998 | Fung et al. | |
| 5,858,205 A | 1/1999 | Huebner | |
| 5,869,743 A * | 2/1999 | Jones | F01N 11/00 73/23.31 |
| 5,877,367 A | 3/1999 | Witte | |
| 5,885,439 A | 3/1999 | Glover | |
| 5,896,743 A | 4/1999 | Griffin | |
| 5,965,473 A | 10/1999 | Sechrist et al. | |
| 6,298,729 B1 | 10/2001 | Locker et al. | |
| 6,380,119 B1 | 4/2002 | Grosch et al. | |
| 6,551,660 B2 | 4/2003 | Holtermann et al. | |
| 6,710,002 B2 | 3/2004 | Grosch et al. | |
| 6,784,132 B1 | 8/2004 | Sechrist | |
| 6,790,802 B1 | 9/2004 | Sechrist | |
| 6,803,029 B2 | 10/2004 | Dieckmann | |
| 6,812,180 B2 | 11/2004 | Fukunaga | |
| 6,881,391 B1 | 4/2005 | Sechrist | |
| 6,974,842 B1 | 12/2005 | Spena et al. | |
| 7,153,801 B2 | 12/2006 | Wu | |
| 7,223,710 B1 | 5/2007 | Sechrist | |
| 7,312,173 B1 | 12/2007 | Yuan et al. | |
| 7,582,272 B2 | 9/2009 | Glova et al. | |
| 7,638,664 B2 | 12/2009 | Peters et al. | |
| 7,868,217 B2 | 1/2011 | Brown et al. | |
| 8,240,129 B2 | 8/2012 | Yezerets et al. | |
| 9,085,736 B2 | 7/2015 | Morrison et al. | |
| 9,822,316 B2 | 11/2017 | Morrison et al. | |
| 9,945,801 B1 * | 4/2018 | Esmaili | C01B 3/384 |
| 2002/0150532 A1 * | 10/2002 | Grieve | B01J 19/2485 423/650 |
| 2005/0203328 A1 | 9/2005 | Glova et al. | |
| 2007/0234708 A1 * | 10/2007 | Jones | F01N 11/00 60/277 |
| 2010/0018901 A1 | 1/2010 | Krupa et al. | |
| 2010/0155293 A1 | 6/2010 | Verstraete et al. | |
| 2010/0160147 A1 | 6/2010 | Wu | |
| 2011/0252867 A1 | 10/2011 | Serra et al. | |
| 2012/0240553 A1 | 9/2012 | LaRose, Jr. et al. | |
| 2014/0030159 A1 | 1/2014 | SerVaas et al. | |
| 2015/0139860 A1 | 3/2015 | Devarakonda | |
| 2015/0167587 A1 * | 6/2015 | Weiss | F02M 26/35 60/605.1 |
| 2018/0106740 A1 * | 4/2018 | Esmaili | C01B 3/384 |
| 2019/0136143 A1 * | 5/2019 | Snell | B01D 3/40 |

FOREIGN PATENT DOCUMENTS

| | | |
|---|---|---|
| EP | 0316727 A1 | 5/1989 |
| WO | 2013062695 A1 | 5/2013 |

OTHER PUBLICATIONS

Foreign communication from a related counterpart application—International Preliminary Report on Patentability, PCT/US2012/056306, dated Apr. 29, 2014, 5 pages.

* cited by examiner

SYSTEM AND METHOD FOR MONITORING A REFORMING CATALYST

REFERENCE TO RELATED APPLICATION

This application is a continuation application of U.S. patent application Ser. No. 15/805,948, filed on Nov. 7, 2017, now U.S. Pat. No. 10,436,762 B2, entitled "System and Method for Monitoring a Reforming Catalyst," the disclosure of which is incorporated herein by reference in its entirety.

FIELD OF THE INVENTION

This disclosure relates generally to a system and method for operating a reforming process. More particularly, the disclosure relates to operating a reforming process while monitoring catalytic performance of a reforming catalyst to determine when corrective action is required.

BACKGROUND OF THE INVENTION

Typical reforming processes can be carried out using a variety of reactors containing reforming catalysts. The reforming process encompasses a number of reactions, which are typically carried out in the presence of a catalyst, such as dehydrocyclization, hydrodecyclization, isomerization, hydrogenation, dehydrogenation, hydrocracking, cracking, etc. Reforming reactions are intended to convert paraffins, naphthenes, and olefins to aromatics and hydrogen. A variety of catalysts are used to carry out the reforming reactions, all of which are subject to deactivation over time. For example, catalyst deactivation can result from poisoning, carbon deposit formation, or other similar processes which necessitate that a corrective action (e.g., catalyst regeneration or replacement with fresh catalyst) be implemented. Any form of corrective action decreases the overall process efficiency of the reforming process and at least temporarily the production capacity. Catalyst replacement cost can be a major economic driver for the reforming process, therefore operators of reforming processes have sought to minimize the frequency of corrective action implementations and extend (e.g., optimize) the useful life of reforming catalysts.

Process monitoring is a key method of extending the useful life of reforming catalysts and includes the use of plant data along with kinetic models to determine catalyst activity and selectivity. Accurate plant data (e.g., reactor inlet temperatures and pressures) is necessary to provide a quality assessment of catalyst performance. However reforming process units face issues including unreliable or inaccurate temperature and pressure indicators, an absence of monitoring instrumentation, and plugging and fouling of monitoring instrumentation. Simplifying the catalyst monitoring process would reduce the error that would be introduced with inaccurate process instrumentation. Furthermore, simplifying the catalyst monitoring process would allow for catalyst performance evaluation in instances where process instrumentation is unreliable or unavailable. Therefore a need exists for improved reforming process monitoring tools.

SUMMARY OF THE INVENTION

Disclosed herein is a method of monitoring catalytic performance of a catalyst used in a reforming process, comprising: a) collecting gaseous component data from the reforming process; b) calculating a gaseous component ratio from the gaseous component data; and c) utilizing the gaseous component ratio to estimate an amount of catalytic activity remaining in the catalyst used in the reforming process, a number of days on stream remaining for the catalyst used in the reforming process, or both.

Also disclosed herein is a method of modeling catalytic performance of a catalyst used in a reforming process, comprising: a) constructing a two-coordinate graph containing a vertical axis for gaseous component ratio data and a horizontal axis for catalyst activity factor data; b) obtaining a set of gaseous component ratio data and a set of catalyst activity factor data for the reforming process; c) representing the set of gaseous component ratio data and the set of catalyst activity factor data upon the two-coordinate graph; and d) constructing a best-fit curve upon the two-coordinate graph, wherein the best-fit curve represents a graphical relationship of the set of gaseous component ratio data and the set of catalyst activity factor data.

Further disclosed herein is a method of modeling catalytic performance of a catalyst used in a reforming process, comprising: a) constructing a two-coordinate graph containing a vertical axis for gaseous component ratio data and a horizontal axis for days-on-stream (DOS) data; b) obtaining a set of gaseous component ratio data and a set of DOS data or the reforming process; c) representing the set of gaseous component ratio data and the set of DOS data upon the two-coordinate graph; and d) constructing a best-fit curve upon the two-coordinate graph, wherein the best-fit curve represents a graphical relationship of the set of gaseous component ratio data and the set of DOS data.

Further disclosed herein is a method of monitoring the catalytic performance of a catalyst used in a reforming process, comprising: a) collecting a gas sample from a gaseous component stream of the reforming process; b) determining a ratio of moles of hydrogen to moles of methane in the gas sample; c) comparing the ratio of moles of hydrogen to moles of methane in the gas sample to a M-EOR value; and d) signaling that the reforming catalyst may be deemed to have reached an end-of-run condition when the ratio of moles of hydrogen to moles of methane in the gas sample is within a threshold range relative to the M-EOR value.

Further disclosed herein is a method of monitoring the catalytic performance of a catalyst used in a reforming process, comprising: a) inputting a catalyst activity end-of-run value into the model constructed as described herein and determining a corresponding mole ratio end-of-run (M-EOR) value; b) collecting a gas sample from a gaseous component stream of the reforming process; c) determining a ratio of moles of hydrogen to moles of methane in the gas sample; d) comparing the ratio of moles of hydrogen to moles of methane in the gas sample to the M-EOR value; and e) signaling that the reforming catalyst may be deemed to have reached an end-of-run condition when the ratio of moles of hydrogen to moles of methane in the gas sample is within a threshold range relative to the M-EOR value.

Further disclosed herein is a method for catalytic reforming comprising: a) providing a hydrocarbon feed stream to one or more reactors; b) contacting the hydrocarbon feed stream with a reforming catalyst in the one or more reactors; c) obtaining a first set of data from the reforming process for each of a plurality of values for each of a CAF, a $H_2/CH_4$ mole ratio, and a DOS; d) modeling a catalytic performance of the reforming catalyst with a catalytic performance model to determine a first best-fit curve based on the plurality of values for each of the CAF and the $H_2/CH_4$ mole ratio, and a second best-fit curve based on the plurality of values for each of the $H_2/CH_4$ mole ratio and the DOS; e) calculating a value for a mole ratio end-of-nm (M-EOR) from a value of a catalyst activity factor end-of-nm (C-EOR) using the first best-fit curve and a value for a DOS end-of-nm (D-EOR) from M-EOR using the second best-fit curve; f) operating the one or more reactors and obtaining a second set of data from the reforming process for values for each of a current $H_2/CH_4$ mole ratio and a current DOS; g) comparing the current $H_2/CH_4$ mole ratio to the M-OER and the current DOS to the D-EOR; and h) signaling that the reforming catalyst may be deemed to have reached an end-of-run condition when the current $H_2/CH_4$ mole ratio is within a threshold range relative to the M-EOR or when the current DOS is within a threshold range relative to the D-EOR.

Further disclosed herein is a method for catalytic reforming comprising: a) providing a hydrocarbon feed stream to one or more reactors and contacting the hydrocarbon feed stream with a reforming catalyst in the one or more reactors; b) modeling catalytic performance of the reforming catalyst with a catalytic performance model by; i) obtaining data from the reforming process for each of a plurality of values for each of a gaseous component ratio, a catalyst activity factor (CAF), and a days on stream (DOS); ii) determining a first best-fit curve based on the plurality of values for each of the gaseous component ratio and the CAF data using a first two coordinate system; iii) determining a second best-fit curve based on the plurality of values for each of the gaseous component ratio and the DOS data using a second two coordinate system; iv) assigning a value for a catalyst activity factor end-of-nm (C-EOR); v) calculating a value for a mole ratio end-of-nm (M-EOR) from a value of the catalyst activity factor end-of-nm (C-EOR) using the first best-fit curve and a value for a DOS end-of-run (D-EOR) from the M-EOR using the second best-fit curve; c) collecting a gas sample from a gaseous component stream of the reforming process; d) calculating a gaseous component ratio in the gas sample; e) comparing the gaseous component ratio in the gas sample to the M-OER and a current DOS to the D-EOR; and f) signaling that the reforming catalyst may be deemed to have reached an end-of-run condition when the gaseous component ratio in the gas sample is within a threshold range relative to the M-EOR or when the current DOS is within a threshold range relative to the D-EOR.

BRIEF DESCRIPTION OF THE DRAWINGS

The following figures form part of the present specification and are included to further demonstrate certain aspects of the present invention. The invention may be better understood by reference to one or more of these figures in combination with the detailed description of specific embodiments presented herein.

Figure 1:
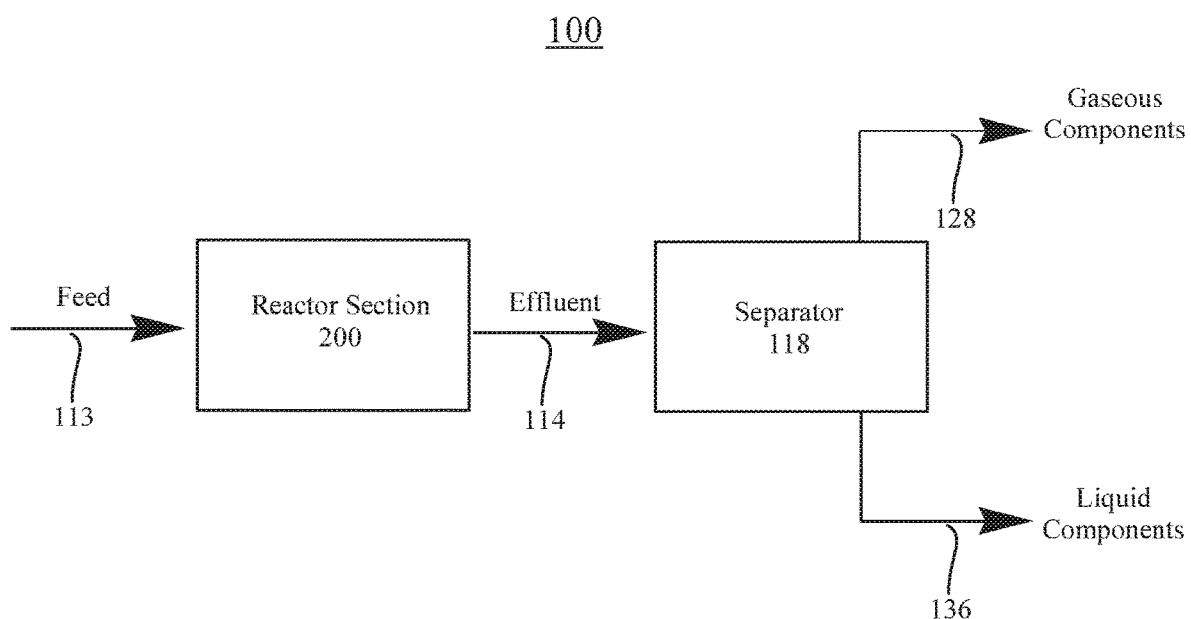
FIG. 1 illustrates an exemplary flow diagram of an aspect of the reforming process of the disclosure.

While the inventions disclosed herein are susceptible to various modifications and alternative forms, only a few specific embodiments have been shown by way of example in the drawings and are described in detail below. The figures and detailed descriptions of these specific embodiments are not intended to limit the breadth or scope of the inventive concepts or the appended claims in any manner. Rather, the figures and detailed written descriptions are provided to illustrate the inventive concepts to a person of ordinary skill in the art and to enable such person to make and use the inventive concepts.

DETAILED DESCRIPTION OF EMBODIMENTS

Disclosed herein are methods and apparatus related to monitoring catalytic performance of a catalyst used in a reforming process. The present disclosure includes methods of monitoring catalytic performance of the catalyst used in the reforming process comprising monitoring a ratio of gaseous components of the reforming process. Also disclosed are methods for modeling catalytic performance of the catalyst used in a reforming process and methods for determining when a corrective action (e.g., restoration of the catalyst) should be administered to the catalyst used in the reforming process.

Disclosed herein are methods of monitoring catalytic performance of a catalyst used in a reforming process. FIG. 1 illustrates a general reforming process 100. At the inlet of the process, a hydrocarbon feed stream is fed through line 113 into reforming reactor section 200 of reforming process 100. Various feedstocks may be suitable for use with reforming processes and generally comprise non-aromatic hydrocarbons. Reforming reactor section 200 may comprise a single reactor or a plurality of reactors as discussed in more detail herein. As is generally understood, a reforming "reaction", typically takes place within a reforming "reactor." The reactor employed in this processes described herein may be any conventional type of reactor that maintains a catalyst within the reactor and can accommodate a continuous flow of hydrocarbon. The catalytic reactor system described herein may comprise a fixed catalyst bed system, a moving catalyst bed system, a fluidized catalyst bed system, or combinations thereof. Within reforming reactor section 200 the single reactor or any reactor of the plurality of reactors may contain a catalyst for carrying out a reforming process. As is known to those of ordinary skill in the art, a suitable reforming catalyst is capable of converting at least a portion of aliphatic, alicyclic, and/or naphthenic hydrocarbons (e.g., non-aromatic hydrocarbons) in the hydrocarbon feed stream to aromatic hydrocarbons. Any catalyst capable of carrying out a reforming process may be used alone or in combination with additional catalytic materials in the reactors. Reactor effluent stream 114 exiting reactor section 200 enters separator 118. Within separator 118 reactor effluent stream 114 is separated into one or more liquid product streams 136 comprising liquid components and one or more net-gas streams 128 comprising gaseous components. The liquid components of liquid product stream 136 comprise about 60 wt % to about 90 wt % aromatics and may be further purified. The gaseous components of net-gas stream 128 comprise, but are not limited to, hydrogen and methane that are produced during the reforming process.

Any catalyst used within reforming reactor section 200 may be characterized by a catalytic performance. The term "catalytic performance" as described herein refers to catalytic activity, catalytic selectivity or combinations thereof as described in more detail herein. A catalyst typically has a finite performance life, which may include one or more cycles of catalyst activity separated by regeneration cycles. For example, as a catalytic process continues over time, the catalyst activity generally decreases. When the catalyst activity reaches a point at which it no longer efficiently catalyzes the process, the catalyst may be at the end of its life or at the end of one of its cycles of catalyst activity. If the catalyst has one or more cycles of catalyst activity remaining, the catalyst can be regenerated to begin a new cycle of catalyst activity. If no additional cycles are available or if the catalyst is not capable of being regenerated, the catalyst life is spent, and the spent catalyst typically will need to be replaced with fresh catalyst. Alternatively, a catalyst may be deemed to have reached an economic end-of-run (EOR) stage when the catalyst displays an unacceptably low catalytic performance compared to an initial catalytic performance (e.g., catalytic performance of fresh or virgin catalyst that has not been previously used in a reforming process or subjected to a restoration process as described herein). In an aspect, a decrease in catalytic performance over time may indicate that an EOR stage of a catalyst has been reached or, alternatively, that an EOR stage of a catalyst is soon to be reached. In a further aspect, a catalyst that has reached an EOR stage may be termed a "spent" catalyst.

Figure 2:
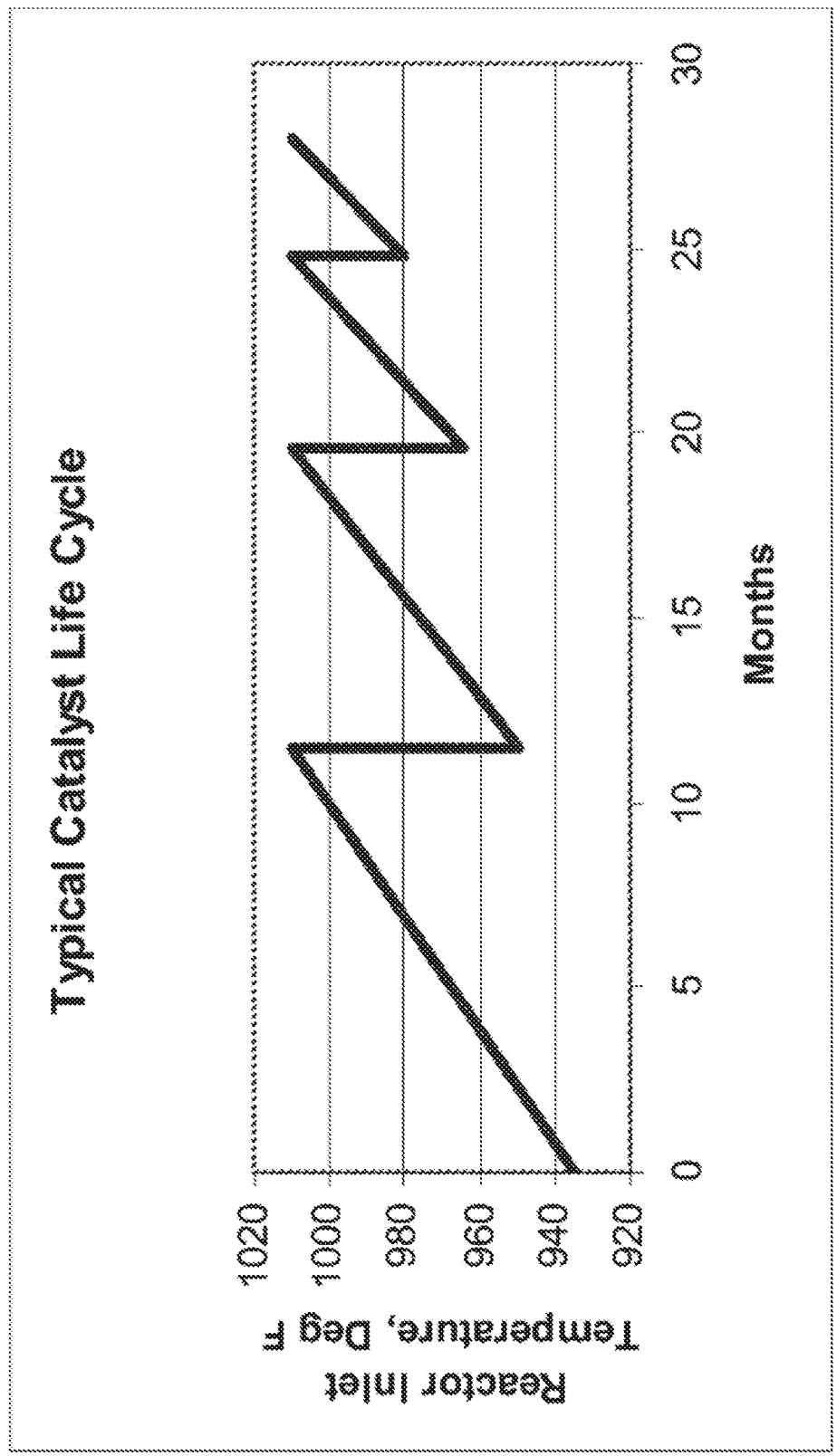
FIG. 2 illustrates an exemplary catalyst life cycle diagram.

FIG. 2 is a hypothetical graph illustrating a general catalyst life cycle for a catalyst having 4 activity cycles and 3 regeneration cycles. The first activity cycle begins at time zero and lasts for many months, and during this cycle the activity of the catalyst decreases as evidenced by an increase in the reactor inlet temperature (as described in more detail herein). The slope of the line represents the fouling rate of the catalyst, i.e., the change in activity over a given period of service time. The reactor inlet temperature continues to increase until it reaches a maximum value (e.g., greater than 1000° F. in FIG. 2), at which time the catalyst may be regenerated (e.g., a regeneration cycle), for example by subjecting the catalyst to a high temperature oxidation (e.g. greater than about 600° F.) to remove carbon build-up such as coking. During the regeneration process, coke may be removed from the catalytic reactor and the catalyst contained therein. The regeneration of the catalyst provides renewed activity to the catalyst (e.g., a new activity cycle) as evidenced by a lower reactor inlet temperature, which is shown by the vertical drops or decreasing steps in FIG. 2. However, when a new cycle is started, the starting reactor inlet temperature is typically higher than for the previous cycle (as shown by the progressively increasing reactor inlet temperature at the start of each new cycle), representing an unrestored loss in overall catalyst activity. Because the catalyst activity is not fully restored after each cycle, the catalyst life is limited by a maximum number of regeneration cycles, for example three as shown by the vertical lines at about 12 months, 19 months, and 24 months in FIG. 2. Furthermore, with each regeneration cycle, the fouling rate (slope) of the catalyst may increase. Thus, regeneration of a catalytic reactor system may also increase the catalyst fouling rate, which would further reduce the total life of a catalyst.

Referring again to the reforming process of FIG. 1, hydrogen is produced throughout conversion of the hydrocarbon feedstock to aromatics. Methane is produced in undesirable side reactions of the hydrocarbon feedstock (e.g., hydrocracking reactions) wherein a portion of the hydrogen produced as described herein is consumed in the undesirable side reactions. As the reforming process proceeds, the frequency of undesirable side reactions increases in response to loss in catalytic performance. In another aspect, the amount of hydrogen within the gaseous component streams of the reforming process correlates well with the amount of methane within the gaseous component streams of the reforming process throughout the course of the reforming process run. In a further aspect, the ratio of the amount of hydrogen to the amount of methane within the gaseous component streams of the reforming process comprises a useful indicator of catalytic performance. In another aspect, the ratio of the moles of hydrogen to the moles of methane within the gaseous component streams of the reforming process comprises a useful indicator of catalytic performance as described in more detail herein.

In an aspect, a method of monitoring catalytic performance of a catalyst used in a reforming process comprises collecting gaseous component data from the reforming process. In another aspect, gaseous component data collected as described herein comprises gaseous component data of a single reactor or alternatively, of a plurality of reactors. In a further aspect, gaseous component data comprises moles of hydrogen and moles of methane present in one or more effluent streams from one or more reactors in the reforming process. In yet a further aspect, gaseous component data may be collected from the reforming process by collecting gas samples from one or more process streams comprising gaseous components (e.g., a gaseous component streams) within the reforming process.

Returning to FIG. 1, gas samples may be collected from gaseous component streams located at various locations within general reforming process 100 via sampling ports located in any convenient piping or tubing within the process. Gas samples may be collected via one or more sampling ports located along reactor effluent stream 114 before passing to separator 118, via one or more sampling ports located along net-gas stream 128, or combinations thereof. In an aspect, a sample is collected from a process stream comprising gaseous components that reflect the molar ratio of hydrogen to methane exiting the reactor upstream of the sampling location. The frequency of gas sample collection may be once daily or any frequency suitable for operation the reforming process as described herein.

In an aspect, gas samples collected from one or more gaseous component streams may be subjected to gas chromatography. In a further aspect, subjecting gas samples to gas chromatography comprises analyzing the identity and amount of distinct gaseous components within the sampled gaseous component stream. In yet another aspect, subjecting gas samples to gas chromatography comprises determining moles of hydrogen and moles of methane within the sampled gaseous component stream. Instrumentation utilized for analyzing gas samples as described herein may comprise any suitable gas chromatography equipment known to one of ordinary skill in the art. In an aspect, commercially available gas-detector tubes or chip measurement systems, e.g., by Gastec® or Drager, may be used to analyze gas samples of the gaseous component stream. In a further aspect, the gas chromatography instrumentation can be on-line, real-time gas chromatography that may be positioned proximate the sampling location and be connected to a computer-implemented monitoring and/or control system, as will be described in more detail herein.

In an aspect, a method of monitoring catalytic performance of a catalyst used in a reforming process comprises calculating a gaseous component ratio from the gaseous component data from the reforming process. In another aspect, the gaseous component ratio calculated as described herein comprises the gaseous component ratio of a single reactor or alternatively, of a plurality of reactors. In an aspect, the gaseous component ratio comprises a ratio of the amounts of distinct components within a gaseous component stream of the reforming process. In a further aspect, a ratio of moles of hydrogen to moles of methane (i.e., $H_2/CH_4$ mole ratio) may be calculated from the gaseous component data from the reforming process. In an aspect, the $H_2/CH_4$ mole ratio (MR) is a dimensionless quantity. In a further aspect, the MR may comprise a value in the range of from about 1 to about 100, alternatively from about 1 to about 50, alternatively from about 2 to about 35, or alternatively from about 5 to about 25.

For example, results of gas chromatography analysis of the gas samples collected from the gaseous component stream as described herein may be utilized to calculate a $H_2/CH_4$ mole ratio present in the sampled gaseous component stream. In a further aspect, the $H_2/CH_4$ mole ratio is calculated within the on-line, real-time gas chromatography instrumentation, or alternatively within a computer-implemented monitoring and/or control system, as will be described in more detail herein. In an aspect, the accuracy of the hydrogen mole data and methane mole data (and the resultant $H_2/CH_4$ mole ratio) may be unaffected by air, water vapor, non-hydrocarbon gaseous components and combinations thereof present in the gaseous component streams or that may be present in a sample thereof (e.g., via inadvertent contamination of the sample).

In a further aspect, the MR will comprise a maximum value (e.g., the MR-SOR as described herein) at the commencement of a reforming process run wherein the MR decreases throughout the course of the reforming process run. In a further aspect the MR may be directly proportional to the amount of catalytic activity within the catalyst, i.e., the MR decreases as the amount of catalytic activity within the catalyst decreases. In yet a further aspect, the MR may be directly proportional to the catalytic lifetime remaining for the catalyst, for example as measured by days on stream (DOS) remaining for the catalyst. Accordingly, as described in more detail herein, a relationship or model of the MR as a function of catalyst activity factor and/or as a function of time (e.g., DOS) may be used to monitor and/or predict the performance of a catalyst used in a reforming process.

Figure 3:
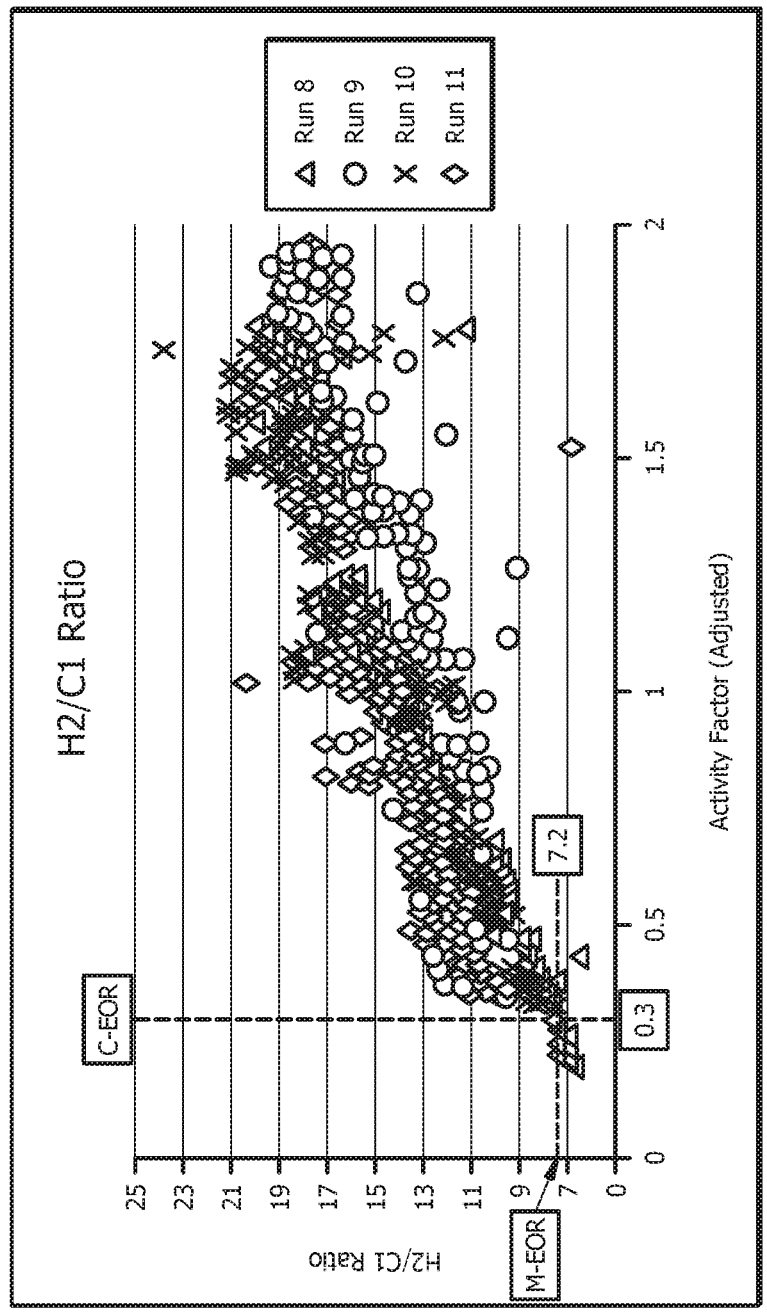
FIG. 3 is an activity factor/mole ratio chart.

In an aspect, catalytic performance of a reforming catalyst may be monitored utilizing a relationship between a gaseous component ratio (e.g., a $H_2/CH_4$ mole ratio) and a catalyst activity factor (CAF), for example as shown in FIG. 3 and discussed in more detail herein. In a further aspect, the CAF is used in combination with a kinetic model and a process simulator to mimic yield structures and process conditions of a reforming process. In an aspect, the yield structures comprise the composition and relative amounts of hydrocarbon products produced by the reforming process. In another aspect, process conditions comprise measurable indicators of the performance of the reforming process, a non-limiting example of which is a process endotherm.

In an aspect, simulation of a reforming process comprises utilization of a kinetic model wherein the kinetic model mimics the outcomes of the hydrocarbon reactions occurring within the reforming process. Examples of hydrocarbon reactions occurring within the reforming process include without limitation the dehydrogenation of cyclohexanes to aromatics, dehydroisomerization of alkylcyclopentanes to aromatics, and hydrocracking reactions which produce light gaseous hydrocarbons, e.g., methane, ethane, propane, and butane. The kinetic model contains a mathematical representation of the Arrhenius rate equation for each hydrocarbon reaction occurring within the reforming process wherein each reaction is represented with a distinct rate equation. The kinetic model further comprises kinetic parameters associated with the rate equations wherein each distinct hydrocarbon reaction comprises a set of kinetic parameters. Examples of kinetic parameters include without limitation an Arrhenius rate constant and an activation energy.

In an aspect, a process simulator is used to simulate operation of a reforming process using the kinetic model. In an aspect, the process simulator mimics the yield structures and process conditions of the reforming process. The process simulator contains the kinetic parameters comprising the kinetic model (and one or more catalyst activity factors associated therewith) and is configured to receive process data of the reforming process and generate simulated process results and simulated data. Non-limiting examples of process data that may be entered the process simulator include reactor inlet temperature, feed composition and feed flow rate. The process simulator applies the kinetic parameters of the kinetic model (and one or more catalyst activity factors associated therewith) to the process data of the reforming process and calculates simulated yield structures and simulated process conditions (e.g., process endotherm) for the reforming process. The values of the simulated yield structures and simulated process conditions may be compared against the actual yield structures and actual process conditions of the reforming process and adjustments made (e.g., adjustments to the one or more catalyst activity factors) to tune the simulation such that simulated results closely match real world results and data. Suitable examples of commercially available process simulators include Sim-Sci Pro/II process simulation software available from Schneider Electric Software of Lake Forrest, Calif. or Aspen Plus® or Aspen HYSYS® process simulation software available from Aspen Technology of Bedford, Mass.

Disclosed herein are methods for modeling catalytic performance of a catalyst used in a reforming process, wherein catalyst activity factors are determined for a simulated reforming process. In an aspect, the simulated reforming process is an existing, operating reforming process such as a lab-scale, bench-scale, pilot plant, or commercial scale reforming process that has been built and is being operated to provide real world operating data, wherein the simulated reforming process is used to closely approximate the real world operating data. In an aspect, the simulated reforming process is a modification to an existing, operating reforming process such as a lab-scale, bench-scale, pilot plant, or commercial scale reforming process that has been built, wherein the simulated reforming process is used to provide predicted operating data of the modified reforming process. In an aspect, the simulated reforming process is a new reforming process (e.g., a new lab-scale, bench-scale, pilot plant, or commercial scale reforming process that has yet to be built), wherein the simulated reforming process is used to provide predicted operating data (e.g., a design basis) of the new reforming process. Such simulated reforming processes may be used to obtain catalyst activity factors (CAF) for further use as described herein (e.g., to determine M-EOR and D-EOR).

In an aspect, simulation of a reforming process comprises utilization of a catalyst activity factor (CAF), for example to adjust one or more parameters of a kinetic model input into simulation software. In an aspect, the CAF is a numeric value which is applied to the kinetic parameters contained within the process simulator. In an aspect, the CAF is utilized to adjust the kinetic model wherein adjustment enables the kinetic model to mimic catalytic performance more accurately. In an aspect, the kinetic model may be adjusted by multiplying the values of the kinetic parameters of the kinetic model by the value of the CAF. In an aspect, adjustments to the kinetic model impact the simulated yield structures and simulated process conditions calculated by the process simulator. In an aspect, the value of the CAF is adjusted in an iterative manner until the simulated yield structures and simulated process conditions calculated by the process simulator correlate well with the actual yield structures and actual process conditions of the reforming process being simulated (e.g., the simulation converges upon a solution closely approximating the conditions specified for the reforming process being simulated).

Figure 4:
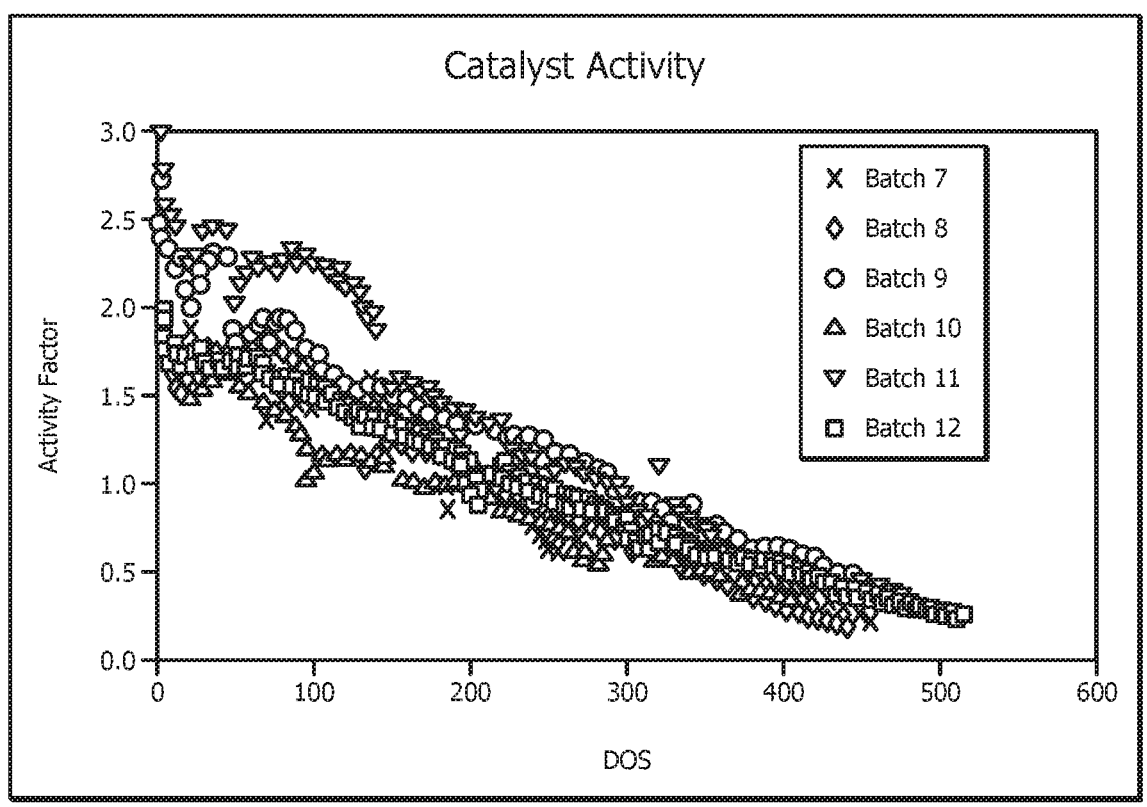
FIG. 4 is a days on stream/activity factor chart.
Figure 5:
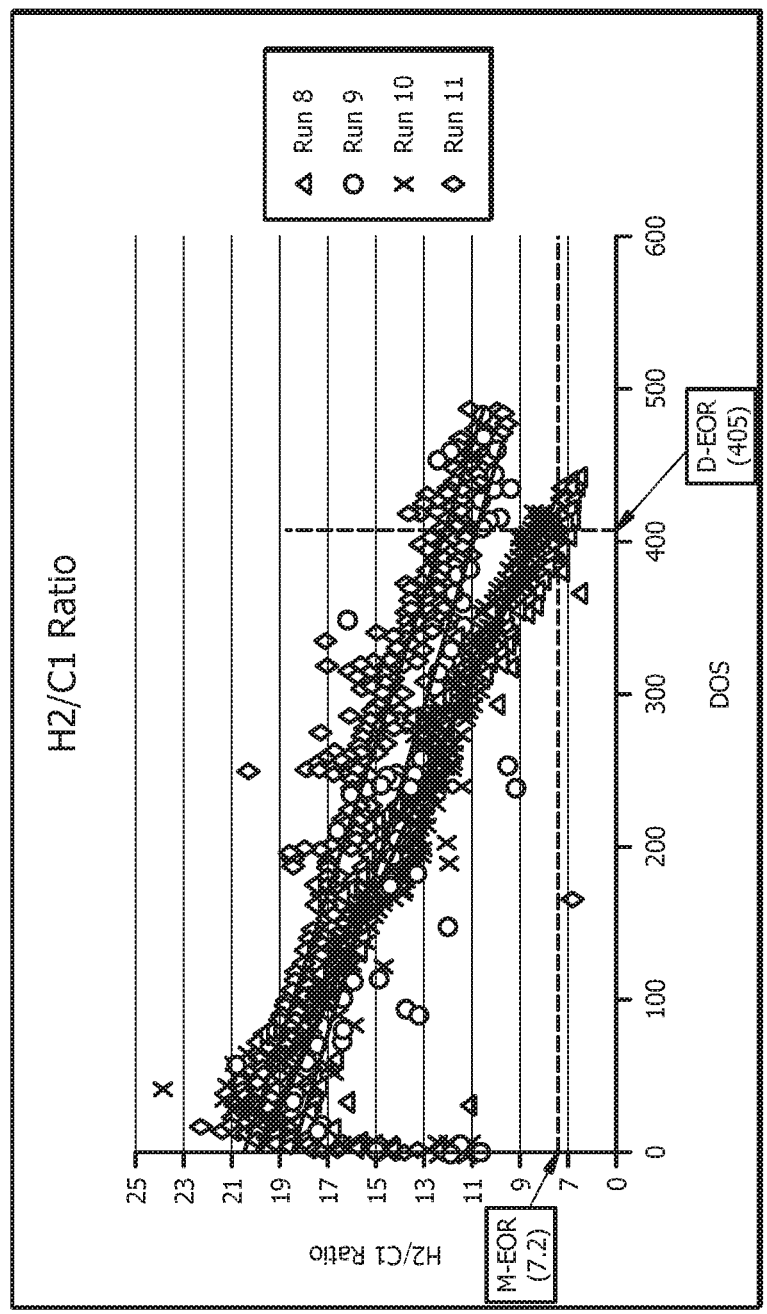
FIG. 5 is a days on stream/mole ratio chart.

In a further aspect, the CAF is applied with equal magnitude to all kinetic parameters of the kinetic model. In a further aspect, the CAF adjusts the kinetic model to closely replicate catalytic performance throughout the course of a reforming process run, for example decreasing over the duration of the simulation proportionally to a decrease in catalytic activity associated with the reforming process being simulated (e.g., an existing commercial plant). In an aspect, a common CAF is used to adjust with equal magnitude one or more kinetic parameters within the kinetic model, wherein the value of the CAF is adjusted in an iterative manner until the simulated yield structures and simulated process conditions calculated by the process simulator correlate well with the actual yield structures and actual process conditions of the reforming process and wherein the CAF decreases over the reforming process run time being simulated. For example, the value of the CAF will decrease over time as catalytic activity decreases throughout the course of the simulated reforming process run. FIG. 4 illustrates a correlation of the decreasing values of Activity Factor (i.e., CAF) as a function of time (e.g., DOS) and shows a characteristic non-linear relationship between CAF and DOS. Furthermore, the decreasing values of CAF may be correlated to decreasing values for a corresponding $H_2/CH_4$ mole ratio (MR) as shown in FIG. 3, and discussed in more detail herein. Likewise, decreasing values of MR as a function of DOS may be correlated as shown in FIG. 5, and discussed in more detail herein. The relationship between MR and CAF (FIG. 3) and the relationship between MR and DOS (FIG. 5) are both about linear and more suitable for monitoring catalytic performance than the non-linear relationship observed between CAF and DOS shown in FIG. 4.

In an aspect, the CAF is dimensionless quantity. In a further aspect, the CAF may comprise a value within the range of from about 0 to about 2 wherein greater levels of catalytic activity correspond to larger CAF values. For example, the CAF value of a fresh catalyst (i.e., a virgin catalyst or a catalyst that has been subjected to a restoration process) will be larger than the CAF value of a spent catalyst wherein the fresh catalyst and the spent catalyst are identical in all other aspects, e.g., the fresh catalyst and the spent catalyst comprise identical types and ratios of metal compounds and support materials as further described herein. In yet another aspect, a decrease in the CAF of the catalyst from a value of 2 to a value of 1 represents a 50% reduction in catalytic activity of the catalyst. In other words a decrease in the CAF value by 1 correlates to a loss of half of the catalytic activity of the catalyst.

Prior to commencement of a reforming process run, the CAF may be assigned a start-of-run (SOR) value wherein the catalyst comprises a fresh catalyst. In a further aspect, the fresh catalyst may be a virgin catalyst or a catalyst that has been subjected to a restoration process. In cases where the fresh catalyst comprises a virgin catalyst, an SOR value of 2, alternatively of about 2, or alternatively of less than about 2 may be assigned. In cases where the fresh catalyst comprises a catalyst that has been subjected to a restoration process, an SOR value of less than about 2 may be assigned. In a further aspect, the CAF will decrease over time from an assigned SOR value (e.g., about 2) to a value less than the assigned SOR value throughout the course of the reforming process run, which may be further correlated to decreasing values for a corresponding $H_2/CH_4$ mole ratios as shown in FIG. 3.

Disclosed herein is a method of monitoring catalytic performance of a catalyst used in a reforming process wherein a correlation of data for the $H_2/CH_4$ mole ratio and catalyst activity factor is used to estimate the amount of catalytic activity remaining in the catalyst. FIG. 3 displays a chart wherein $H_2/CH_4$ mole ratio (MR) baseline data for a reforming process is plotted against catalyst activity factor (CAF) determined from a simulation of the reforming process corresponding to the baseline data. For example, as shown in FIG. 3, four sets of baseline MR data are provided (Run 8-Run 11), which are based on independent historical runs of a reforming process. In an alternative embodiment, the baseline MR data may be theoretical data for a modified reforming process or a design basis for a new reforming process. Each of these four sets of baseline MR data may be used in conjunction with a process simulation as described herein to obtain corresponding CAF values. In an aspect, the yield structures and process conditions (e.g., the selected baseline MR data such as a historical run) correlate well with the yield structures and process conditions (e.g., MR data) of the simulation of the reforming process (that is, the simulation closely approximates the MR baseline data used in FIGS. 3 and 5). The MR versus CAF data associated with any one data set (e.g., historical run) is selected and used to construct a best-fit curve upon the chart, wherein the best-fit curve represents a graphical relationship (e.g., a linear relationship) of the MR versus CAF data for the selected data set (e.g., historical run). A CAF end-of-run (C-EOR) value is assigned wherein the C-EOR value is a CAF value indicative of a catalyst that has reached an EOR stage and wherein the C-EOR value is represented upon the chart as a vertical line, e.g., FIG. 3 displays a C-EOR value of about 0.3. A point of intersection of the best-fit curve with the vertical line is determined and the vertical axis value of the point of intersection is assigned as a $H_2/CH_4$ mole ratio end-of-run (M-EOR) value wherein the M-EOR value is a MR indicative of a catalyst that has reached an EOR stage. In a non-limiting example the Run 8 data of FIG. 3 is selected and used to construct a best-fit curve upon the chart wherein the value of the point of intersection of the best-fit curve with the vertical line contains an M-EOR value of about 7.2.

Disclosed herein is a method of monitoring catalytic performance of a catalyst used in a reforming process wherein a correlation of data for the $H_2/CH_4$ mole ratio and days-on-stream is used to estimate a number of days on stream remaining for the catalyst. FIG. 5 displays a chart wherein $H_2/CH_4$ mole ratio (MR) baseline data for a reforming process is plotted against days-on-stream (DOS), wherein the DOS data may be actual data corresponding to actual MR baseline data (e.g., corresponding real world data from a historical run) or the DOS data may be theoretical data corresponding to theoretical MR baseline data (e.g., corresponding design basis data used to simulate a new reforming process). For example, as shown in FIG. 5, four sets of baseline MR data are provided (Run 8-Run 11), which are based on independent historical runs of a reforming process (and the four data sets in FIG. 5 correspond to the four data sets of FIG. 3). In an alternative embodiment, the DOS data may be theoretical data for a modified reforming process or a design basis for a new reforming process, as noted previously. The MR versus DOS data associated with any one data set (e.g., historical run) is selected and used to construct a best-fit curve upon the chart, wherein the best-fit curve represents a graphical relationship (e.g., a linear relationship) of the MR versus DOS data for the selected data set (e.g., historical run). A $H_2/CH_4$ mole ratio end-of-run (M-EOR) value is assigned and represented upon the chart as a horizontal line, wherein the M-EOR value is a MR indicative of a catalyst that has reached an EOR stage. In an aspect, the M-EOR value is assigned as previously described herein with reference to FIG. 3 by using a chart containing data for MR and CAF, wherein MR data is plotted against CAF data (e.g., the M-EOR value is assigned a value of about 7.2 as described previously herein from the Run 8 data). Returning to FIG. 5, a point of intersection of the best-fit curve with the horizontal line (e.g., M-EOR=about 7.2) may be determined and the horizontal axis value of the point of intersection may be assigned as a D-EOR value. In a non-limiting example, the Run 8 data is used to construct a best-fit curve upon the chart in FIG. 5 and a horizontal line correlating to a M-EOR value of about 7.2 is drawn on the chart. The point of intersection of the best-fit curve with the horizontal line contains a D-EOR value of about 405 days. In an aspect, the D-EOR is a prediction of the total number of days a catalyst will be utilized continuously in a reforming process before catalytic performance reaches an EOR stage. In an aspect, the current DOS value (i.e., the number of days during which the reforming process has been operated) of a reforming process is subtracted from the D-EOR value to estimate the number of days on stream remaining for the catalyst. For example, if the D-EOR is 405 days as described previously, and the process has been in continuous operation for 150 days, then the predicted or estimated number of days on stream remaining for the catalyst is 405 days-150 days=255 days.

Disclosed herein are methods for modeling catalytic performance of a catalyst used in a reforming process. The methods of modeling disclosed herein may be applied to a new reforming process wherein the new reforming process comprises feed compositions, yield structures, process plant location or combinations thereof that have not been previously utilized within a reforming process. In an aspect, the new reforming process comprises a proposed or planned new commercial scale reforming process. In an aspect, a new kinetic model of the new reforming process is developed wherein the new kinetic model mimics the outcomes of the hydrocarbon reactions occurring within the new reforming process. In an aspect plant process data is used to develop the new kinetic model wherein the plant process data is obtained from a reforming process plant (e.g., pilot scale plant or commercial scale plant) that has previously conducted an identical or closely related version of the new reforming process. In a further aspect, a process simulator is configured with the new kinetic mode and theoretical process data (e.g., a design basis) of the new forming process. In a further aspect the process simulator calculates simulated yield structures and simulated process conditions of the new reforming process. In a further aspect, the process simulator performs an identical set of functions upon the process data of the new reforming process as the set of functions that are performed for a reforming process as described previously herein. In an aspect, a catalyst activity factor (CAF) is utilized to adjust the kinetic model of the new reforming process wherein the CAF of the new reforming process comprises the same functions as the CAF utilized in a reforming process as described previously herein. The CAF of the new reforming process may be closely related to a CAF used with a kinetic model associated with the reforming process plant that has previously conducted an identical or closely related version of the new reforming process. In an aspect, the value of the CAF is adjusted in an iterative manner until the simulated yield structures and simulated process conditions calculated by the process simulator for the new reforming process correlate well with the actual yield structures and actual process conditions of the reforming process plant that has previously conducted an identical or closely related version of the new reforming process. In another aspect, the value of CAF is adjusted in an iterative manner until the simulated yield structures and simulated process conditions calculated by the process simulator for the new reforming process correlate well with the theoretical yield structures and theoretical process conditions (e.g., the design basis) of the new reforming process. In yet a further aspect, the CAF developed as described herein is utilized in modeling catalytic performance of the catalyst of the new reforming process, for example as described with reference to FIGS. 3 and 5 above.

In an aspect of modeling catalytic performance of a catalyst used in a new reforming process, a set of gaseous component ratio data and a set of CAF data for a reforming process are obtained, and a two-coordinate graph (or mathematical equation representing same) is constructed wherein the graph comprises a vertical axis for gaseous component ratio data (e.g., a $H_2/CH_4$ mole ratio) and a horizontal axis for catalyst activity factor (CAF) data. For example, gaseous component ratio data and CAF data are collected periodically, and the collected set of gaseous component ratio data and the collected set of CAF data are represented upon the graph. In yet a further aspect, a best-fit curve is constructed upon the graph, wherein the best-fit curve represents a graphical relationship (or mathematical equation representing same) of the set of gaseous component ratio data and the set of CAF data.

In an aspect, modeling catalytic performance of the reforming catalyst further comprises assigning a catalyst activity end-of-nm (C-EOR) value and representing the C-EOR value as a vertical line upon the graph, as shown in FIG. 3. In an aspect, the C-EOR value is a CAF value indicative of a catalyst that has reached an EOR stage. In an aspect, the C-EOR value is obtained from a previously conducted reforming process (e.g., historical data for CAF values present at the end of one or more historical runs of an existing reforming process). In cases where the reforming process being modeled is a new reforming process the C-EOR value is obtained from a previously conducted reforming process that is an identical or closely related version of the new reforming process. In still a further aspect the C-EOR value for the new reforming process may be obtained from the same reforming process that provided the process data utilized to develop the new kinetic model of the new reforming process. In a further aspect, a point of intersection of the best-fit curve with the vertical line is determined and the vertical axis value of the point of intersection is assigned as a gaseous component ratio end-of-run value. In an aspect, the gaseous component ratio end-of-run value is a gaseous component ratio indicative of a catalyst that has reached an EOR stage.

In an aspect, the gaseous component ratio data utilized as described herein comprises a ratio of moles of hydrogen to moles of methane (i.e., a $H_2/CH_4$ mole ratio) wherein the gaseous component ratio data is obtained via gas chromatography of one or more samples obtained from a gaseous component stream. In a further aspect, the $H_2/CH_4$ mole ratio is calculated by collecting gas samples from the process streams of a reforming process as described herein and subjecting the samples to gas chromatography as described herein. In a further aspect, the gaseous component ratio end-of-run value is a $H_2/CH_4$ mole ratio end-of-run (M-EOR) value wherein the M-EOR value is a $H_2/CH_4$ mole ratio indicative of a catalyst that has reached an EOR stage, which may be determined as described herein with reference to FIG. 3 and/or determined on the basis of historical operating data for a reforming process (e.g., a measurement of $H_2/CH_4$ mole ratio occurring proximate in time (e.g., within an hour, day, or week) with a determination that a catalyst has reached an end of run condition).

In an aspect, the best-fit curve utilized as described herein is a chart or graph constructed from gaseous component ratio data and catalyst activity factor data as described herein. In a further aspect, the best-fit curve utilized as described herein is a mathematical equation (e.g., a linear equation) constructed from gaseous component ratio data and catalyst activity factor data as described herein. In an aspect the graphical relationship of the best-fit curve described herein is about linear. In a further aspect, the graphical relationship is about linear near the start of the reforming process and remains about linear during the operating run-time of the reforming process. In yet a further aspect, the graphical relationship remains about linear near extreme end-of-run conditions wherein extreme end-of-run conditions comprise conditions approaching an economic end-of run (EOR) stage. In an aspect, the best-fit curve utilized as described herein is constructed from historical reforming process data wherein the historical reforming process data is obtained from a commercial scale reforming process plant or a pilot scale reforming process plant. In a further aspect, the historical reforming process data comprises process data obtained from a process identical, nearly identical or closely related to the reforming process being evaluated.

In a further aspect of modeling catalytic performance of a catalyst used in a reforming process, a two-coordinate graph (or mathematical equation representing same) is constructed wherein the graph comprises a vertical axis for gaseous component ratio data and a horizontal axis for days-on-stream (DOS) data. In a further aspect, a set of gaseous component ratio data and a set of DOS data for a reforming process are obtained. For example, gaseous component ratio data and DOS data are collected periodically, and the collected set of gaseous component ratio data and the collected set of DOS data are represented upon the graph. In yet a further aspect, a best-fit curve is constructed upon the graph, wherein the best-fit curve represents a graphical relationship (or mathematical equation representing same) of the set of gaseous component ratio data and the set of DOS data.

In an aspect, modeling catalytic performance of the reforming catalyst further comprises assigning a gaseous component ratio end-of-run value (e.g., M-EOR) and representing the gaseous component ratio end-of-run value as a horizontal line upon the graph, as shown in FIG. 5. In an aspect, the gaseous component ratio data utilized as described herein comprises a ratio of moles of hydrogen to moles of methane (i.e., a $H_2/CH_4$ mole ratio) wherein the gaseous component ratio data is obtained via gas chromatography of one or more samples obtained from a gaseous component stream as described in detail herein. In an aspect, the gaseous component ratio end-of-run value is a gaseous component ratio indicative of a catalyst that has reached an EOR stage (e.g., a M-EOR). In an aspect, the gaseous component ratio end-of-run value is obtained as described herein using a chart (e.g., FIG. 3) or equation representing gaseous component ratio data and CAF data from the reforming process wherein gaseous component ratio data is plotted against CAF data. In a further aspect, a point of intersection of the best-fit curve with the horizontal line is determined and the horizontal axis value of the point of intersection is assigned as a DOS end-of-run (D-EOR) value. In an aspect, the D-EOR value is a prediction of the total number of days the reforming process will be operated before catalytic performance reaches an EOR stage.

In an aspect, the best-fit curve utilized as described herein is a chart or graph constructed from gaseous component ratio data and DOS data as described herein. In a further aspect, the best-fit curve utilized as described herein is a mathematical equation (e.g., a linear equation) constructed from gaseous component ratio data and DOS data as described herein. In an aspect the graphical relationship of the best-fit curve described herein is about linear. In a further aspect, the graphical relationship is about linear near the start of the reforming process and remains about linear during the operating run-time of the reforming process. In yet a further aspect, the graphical relationship remains about linear near extreme end-of-run conditions wherein extreme end-of-run conditions comprise conditions approaching an economic end-of-run (EOR) stage. In an aspect, the best-fit curve utilized as described herein is constructed from historical reforming process data wherein the historical reforming process data is obtained from a commercial scale reforming process plant or a pilot scale reforming process plant. In a further aspect, the historical reforming process data comprises process data obtained from a process identical, nearly identical or closely related to the reforming process being evaluated.

Disclosed herein is a method of monitoring catalytic performance of a catalyst used in a reforming process comprising collecting a gas sample from a gaseous component stream of the reforming process. Referring to FIG. 1, gas samples may be collected from gaseous component streams located at various locations within general reforming process 100 via sampling ports located in any convenient piping or tubing within the process. Gas samples may be collected via one or more sampling ports located along reactor effluent stream 114 before passing to separator 118, via one or more sampling ports located along net-gas stream 128, or combinations thereof. The frequency of gas sample collection may be once daily or any frequency suitable for monitoring the operation the reforming process as described herein. In an aspect, a sample is collected from a process stream comprising gaseous components that reflect the molar ratio of hydrogen to methane exiting the reactor upstream of the sampling location. In an aspect, the method of monitoring catalytic performance further comprises determining a ratio of moles of hydrogen to moles of methane (i.e., $H_2/CH_4$ mole ratio) in the gas sample. Gas samples collected as described herein may be subjected to gas chromatography wherein moles of hydrogen and moles of methane within the gas sample are determined. In a further aspect, the results of gas chromatography analysis of the gas samples may be utilized to calculate a $H_2/CH_4$ mole ratio. Instrumentation utilized for analyzing gas samples as described herein may comprise any suitable gas chromatography equipment known to one of ordinary skill in the art. In an aspect, commercially available gas-detector tubes or chip measurement systems, e.g., by Gastec® or Drager, may be used to analyze gas samples of the gaseous component stream. In yet a further aspect, a method of monitoring the catalytic performance of a catalyst used in a reforming process further comprises a comparison of the $H_2/CH_4$ mole ratio in the gas sample obtained as described herein to a M-EOR value obtained as described herein. In an aspect, the M-EOR value is obtained as described herein using a chart (e.g., FIG. 3) or mathematical equation containing $H_2/CH_4$ mole ratio data and CAF data from the reforming process wherein gaseous component ratio data is plotted against CAF data. In still another aspect, a method of monitoring the catalytic performance of a catalyst used in a reforming process further comprises signaling that the reforming catalyst may be deemed to have reached an end-of-run condition when the $H_2/CH_4$ mole ratio in the gas sample is within a threshold range relative to the M-EOR value. Alternatively, signaling that the reforming catalyst may be deemed to have reached an end-of-run condition occurs when the $H_2/CH_4$ mole ratio in the gas sample is from about 85% to about 115%, alternatively from about 95% to about 105%, or alternatively from about 95% to about 98% of the M-EOR value. In yet a further aspect, a method of monitoring the catalytic performance of a catalyst used in a reforming process further comprises using the $H_2/CH_4$ mole ratio in the gas sample to estimate number of days on stream remaining for the catalyst, for example as described herein with reference to FIG. 5. In still another aspect, a method of monitoring the catalytic performance of a catalyst used in a reforming process further comprises signaling that the reforming catalyst may be deemed to have reached an end-of-nm condition when the $H_2/CH_4$ mole ratio in the gas sample is within a threshold range relative to the estimated number of days on stream remaining for the catalyst.

In an aspect, a method of monitoring the catalytic performance of a catalyst used in a reforming process further comprises initiating a corrective action upon the reforming catalyst when the $H_2/CH_4$ mole ratio in the gas sample is within a threshold range relative to the M-EOR value. Alternatively, initiating a corrective action upon the reforming catalyst occurs when the $H_2/CH_4$ mole ratio in the gas sample is from about 85% to about 115%, alternatively from about 95% to about 105%, or alternatively from about 95% to about 98% of the M-EOR value. In an aspect, the corrective action comprises halting operation of the reforming process, replacing all or a portion of the reforming catalyst, regenerating all or a portion of the reforming catalyst, or combinations thereof.

In an aspect, a method of monitoring the catalytic performance of a catalyst used in a reforming process further comprises initiating a corrective action upon the reforming catalyst when the estimated number of days on stream remaining for the catalyst is equal to or below a threshold value. Alternatively, initiating a corrective action upon the reforming catalyst occurs when the estimated number of days on stream remaining for the catalyst is equal to or less than about 60, 45, 35, 28, 21, 14, 7, 6, 5, 4, 3, 2, or 1 days. In an aspect, the corrective action comprises halting operation of the reforming process, replacing all or a portion of the reforming catalyst, regenerating all or a portion of the reforming catalyst, or combinations thereof.

Disclosed herein is a model wherein the model is generated by constructing a two-coordinate graph (or mathematical equation representing same) wherein the graph comprises a vertical axis for gaseous component ratio data and a horizontal axis for catalyst activity factor data. In an aspect, the model is further generated by obtaining a set of gaseous component ratio data and a set of catalyst activity factor (CAF) data for a reforming process. In an aspect, gaseous component ratio data and corresponding CAF data for the reforming process are collected periodically. In a further aspect, the set of gaseous component ratio data and the set of CAF data are represented upon the graph. In yet a further aspect, a best-fit curve is constructed upon the graph, wherein the best-fit curve represents a graphical (or mathematical) relationship (such as a linear relationship) of the set of gaseous component ratio data and the set of CAF data. In yet a further aspect, the best-fit curve obtained as described herein is represented by a mathematical function wherein the mathematical function comprises the model as disclosed herein and wherein the model comprises a relationship between gaseous component ratio data and CAF data.

Disclosed herein is a method of monitoring catalytic performance of a catalyst used in a reforming process wherein the method comprises the use of the model for the relationship between gaseous component ratio data and CAF data. In an aspect, the method comprises inputting a catalyst activity end-of-run value into the model and determining a corresponding mole ratio end-of-run (M-EOR) value. In a further aspect the model comprises a mathematical function representing the best-fit curve wherein the best-fit curve represents a graphical relationship (e.g., a linear relationship) of the gaseous component ratio data and the CAF data obtained from the reforming process as described herein. In an aspect, the method further comprises collecting a gas sample from a gaseous component stream of the reforming process. The gas sample is collected as previously described herein wherein frequency of gas sample collection may be once daily or any frequency suitable for monitoring the operation the reforming process as described herein. In an aspect, a gas sample is collected from a process stream comprising gaseous components that reflect the molar ratio of hydrogen to methane exiting the reactor upstream of the sampling location. In another aspect, the method further comprises determining a ratio of moles of hydrogen to moles of methane (i.e., $H_2/CH_4$ mole ratio) in the gas sample. Gas samples collected as described herein may be subjected to gas chromatography wherein moles of hydrogen and moles of methane within the gas sample are determined by gas chromatography. In another aspect, the method comprises utilizing the results of gas chromatography analysis of the gas samples to calculate a $H_2/CH_4$ mole ratio as described previously herein. In yet a further aspect, the method further comprises comparison of the $H_2/CH_4$ mole ratio in the gas sample obtained as described herein to the M-EOR value obtained as described herein. In an aspect, the M-EOR value is obtained by inputting a catalyst activity end-of-run value into the model wherein the model comprises a relationship between gaseous component ratio data and CAF data and determining a corresponding M-EOR value. In still another aspect, the method further comprises signaling that the reforming catalyst may be deemed to have reached an end-of-nm condition when the $H_2/CH_4$ mole ratio in the gas sample is within a threshold range relative to the M-EOR value. In an aspect, a method of monitoring the catalytic performance of a catalyst used in a reforming process further comprises initiating a corrective action upon the reforming catalyst when the $H_2/CH_4$ mole ratio in the gas sample is within a threshold range relative to the M-EOR value.

Described herein is a model wherein the model is generated by constructing a two-coordinate graph (or mathematical equation representing same) wherein the graph comprises a vertical axis for gaseous component ratio data and a horizontal axis for days-on-stream (DOS) data. In an aspect, the model is further generated by obtaining a set of gaseous component ratio data and a set of DOS data for a reforming process. In an aspect, gaseous component ratio data and corresponding DOS data for the reforming process are collected periodically. In a further aspect, the set of gaseous component ratio data and the set of DOS data are represented upon the graph. In yet a further aspect, a best-fit curve is constructed upon the graph, wherein the best-fit curve represents a graphical (or mathematical) relationship (such as a linear relationship) of the set of gaseous component ratio data and the set of DOS data. In yet a further aspect, the best-fit curve obtained as described herein is represented by a mathematical function wherein the mathematical function comprises the model as disclosed herein and wherein the model comprises a relationship between gaseous component ratio data and DOS data.

Disclosed herein is a method of monitoring catalytic performance of a catalyst used in a reforming process wherein the method comprises use of a model for the relationship between gaseous component ratio data and DOS data. In an aspect, the method comprises inputting a mole ratio end-of-run (M-EOR) value into the model and determining a corresponding DOS end-of-run (D-EOR) value. In a further aspect, the model comprises a mathematical function representing the best-fit curve wherein the best-fit curve represents a graphical relationship (e.g., a linear relationship) of the gaseous component ratio data and the DOS data obtained from the reforming process as described herein. In another aspect, the method further comprises comparison of the current DOS data (the present number of days on stream that have elapsed since the start of run for the reforming catalyst) to the D-EOR value obtained as described herein to determine an estimated number of days on stream remaining for the catalyst. In an aspect, the D-EOR value is obtained by inputting a M-EOR value into the model wherein the model comprises a relationship between gaseous component ratio data and DOS data and determining a corresponding D-EOR value. In still another aspect, the method further comprises signaling that the reforming catalyst may be deemed to have reached an end-of-run condition when the current DOS data is within a threshold range relative to the D-EOR value. In an aspect, a method of monitoring the catalytic performance of a catalyst used in a reforming process further comprises initiating a corrective action upon the reforming catalyst when the estimated number of days on stream remaining for the catalyst is equal to or below a threshold value.

Several advantages are created when catalytic performance of a reforming process is monitored by analysis of a $H_2/CH_4$ mole ratio of gaseous component streams. Gas chromatography is the primary analytical method, and in some instances may be the only analytical method. Monitoring catalytic performance as described herein is performed without the need for pressure sensors, temperature sensors and the associated signal processing equipment, thereby reducing operating costs and errors associated with the collection of process data. The accuracy of the $H_2/CH_4$ mole ratio data is not affected by air, water vapor, non-hydrocarbon gaseous components or combinations thereof that may be present in the gaseous component streams of the reforming process or samples taken thereof (for example, samples contaminated with ambient air).

A primary advantage is the ability to optimize the useful life of the reforming catalyst. Catalyst replacement cost can be a major economic driver for reforming processes and extending the useful life of reforming catalysts is essential to maintain the economic efficiency of the reforming process. Halting operation of the reforming process, (e.g., to replace a spent catalyst), is referred to as a "turnaround" and scheduling the turnaround occurs far in advance of reaching an EOR stage. If the catalyst is removed from the reforming process before reaching the EOR stage the useful life of the reforming catalyst will be reduced. Conversely, if the reforming catalyst remains within the reforming process after reaching the EOR stage the feedstock will not be converted properly and the economic efficiency of the reforming process will be reduced. Accurate prediction of when the EOR stage will occur improves the timing of the concurrence of the turnaround with the EOR stage. A best-fit curve of the relationship between $H_2/CH_4$ mole ratio (MR) and days on stream (DOS) shown in FIG. 5 and described herein, is about linear and remains about linear near extreme EOR conditions. The about linear behavior of the best-fit curve of the MR vs. DOS relationship can improve the accuracy of EOR prediction and the efficiency of turnaround planning. Conversely, a best-fit curve of the relationship between catalyst activity factor (CAF) and DOS shown in FIG. 4 and described herein, is non-linear and does not facilitate accurate EOR prediction.

The useful life of a catalyst is optimized when the amount of time the catalyst remains within the reforming process is optimized. The latter is optimized when minimal errors occur in determining whether an EOR stage has been reached and/or in determining when an EOR stage will be reached. Errors in the determinations are impacted by shortcomings in the process instrumentation used to collect process data. Minimal process instrumentation is used when the monitoring tool comprises the $H_2/CH_4$ mole ratio measured against an M-EOR value, as described herein, therefore minimal error is introduced when this monitoring tool is used. Conversely, other methods of monitoring catalytic performance include the use of pressure sensors and temperature sensors, both of which may be particularly prone to error. Accurate monitoring of catalytic performance as described herein can optimize the useful life of the catalyst and minimize the costs of catalyst replacement.

In a further advantage, monitoring catalytic performance is simplified by reducing the amount of requisite process instrumentation, therefore monitoring can be performed by individuals not familiar with the complex aspects of catalyst activity factors, calculations of a process simulator, etc. Another advantage is that catalytic performance can be monitored at reforming processing units that are equipped with minimal process instrumentation. Access to gaseous component streams which facilitate collection of gas samples and gas chromatography thereof as described herein are all that is needed in order to achieve effective monitoring.

A further advantage is that catalytic performance of the catalyst of one or more reforming processes comprising one or more feed stock type, one or more set of operating conditions, one or more operating location or combinations thereof may be monitored and/or modeled utilizing $H_2/CH_4$ mole ratio data. Also, the best-fit curves utilized as described herein of reforming processes comprising a variety of feed stocks, a variety of operating conditions, a variety of operating sites or combinations thereof remains about linear while carrying out the reforming processes. Thus, comparison factors may be formulated and applied to the $H_2/CH_4$ mole ratio data of various process units comprising one or more feedstock types, one or more set of operating conditions, one or more operating locations or combinations thereof, wherein the comparison factor may enable a meaningful comparison of catalytic performance among the various process units.

Figure 6:
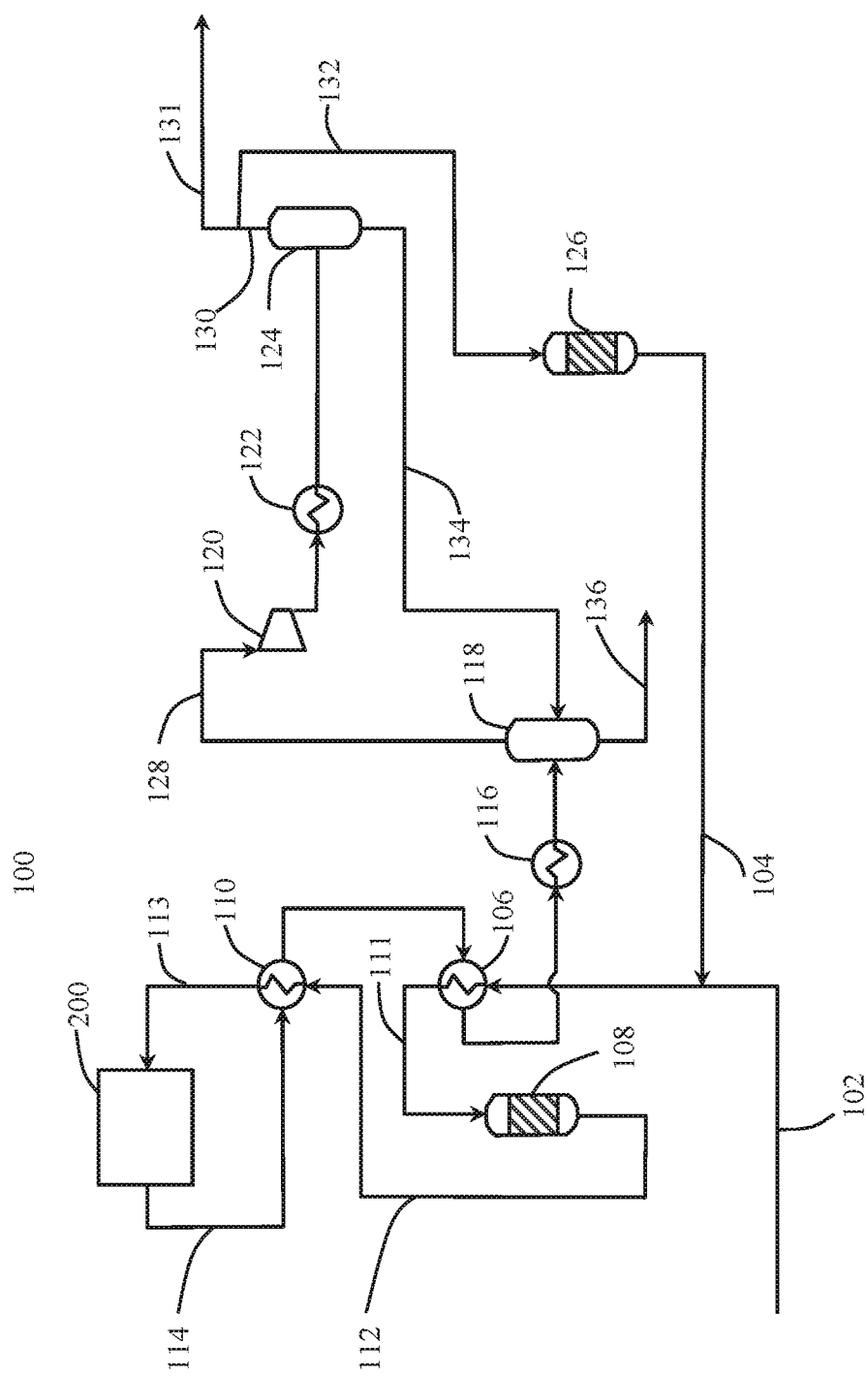
FIG. 6 illustrates a flow diagram of an aspect of a reforming process of the disclosure.

For example, the various methods of monitoring catalytic performance of a catalyst may be used for a general reforming process 100 such as shown in FIG. 6. At the inlet of the process, the hydrocarbon stream is fed through line 102. Various feedstocks may be suitable for use with reforming processes and generally comprise non-aromatic hydrocarbons. The feed to the reforming system comprising an aromatization system can be a mixture of hydrocarbons comprising $C_6$ to $C_8$ hydrocarbons containing up to about 10 percent by weight (i.e., wt %) and alternatively up to about 15 wt % of $C_5$ and lighter hydrocarbons ($C_5^-$) and containing up to about 10 wt % of $C_9$ and heavier hydrocarbons ($C_9^+$). This would include streams boiling within the 70° F.-450° F. temperature range, alternatively from about 120° F. to about 400° F. In an embodiment, the hydrocarbon stream may have a sulfur content ranging from less than 200 parts per billion by weight (i.e., ppbw), alternatively less than 100 ppbw, alternatively from about 10 parts per billion by weight (ppbw) to about 100 ppbw. Examples of suitable feedstocks include straight-run naphthas from petroleum refining or fractions thereof which have been hydrotreated to remove sulfur and other catalyst poisons. Also suitable are synthetic naphthas or naphtha fractions derived from other sources such as coal, natural gas, or from processes such as Fischer-Tropsch processes, fluid catalytic crackers, and hydrocrackers. While not shown in FIG. 6, various upstream hydrocarbon pretreatment steps may be used to prepare the hydrocarbon for the reforming process. For example, hydrotreating may be used to remove catalyst poisons such as sulfur. Contacting the hydrocarbon with a massive nickel catalyst, for example, prior to the reforming reaction may also protect against failure of the hydrotreating system.

The hydrocarbon stream passing through line 102 may be combined with a recycle stream 104, which may contain hydrogen, before passing to a first heat exchanger 106. After passing through the first heat exchanger 106, the hydrocarbon stream passes to the sulfur removal system 108 through line 111. The sulfur removal system 108 may be used to reduce the amount of sulfur in the hydrocarbon stream and may comprise any suitable sulfur removal system capable of removing sulfur from the hydrocarbon stream. In an embodiment, the sulfur removal system 108 may comprise one or more vessels that allow the hydrocarbon stream to pass as a fluid through a sulfur removal system comprising a sulfur converter containing, a group VIII metal and a sulfur adsorber. The sulfur removal system 108 may also act as a precaution or backup in case any upstream hydrotreating system fails or has an operating upset. After passing through the sulfur removal system 108, the hydrocarbon stream may pass through line 112 to a second heat exchanger 110 designed to further adjust the temperature of the hydrocarbon stream. The hydrocarbon stream may then pass through line 113 to the reforming reactor section 200 of reforming process 100.

Figure 7:
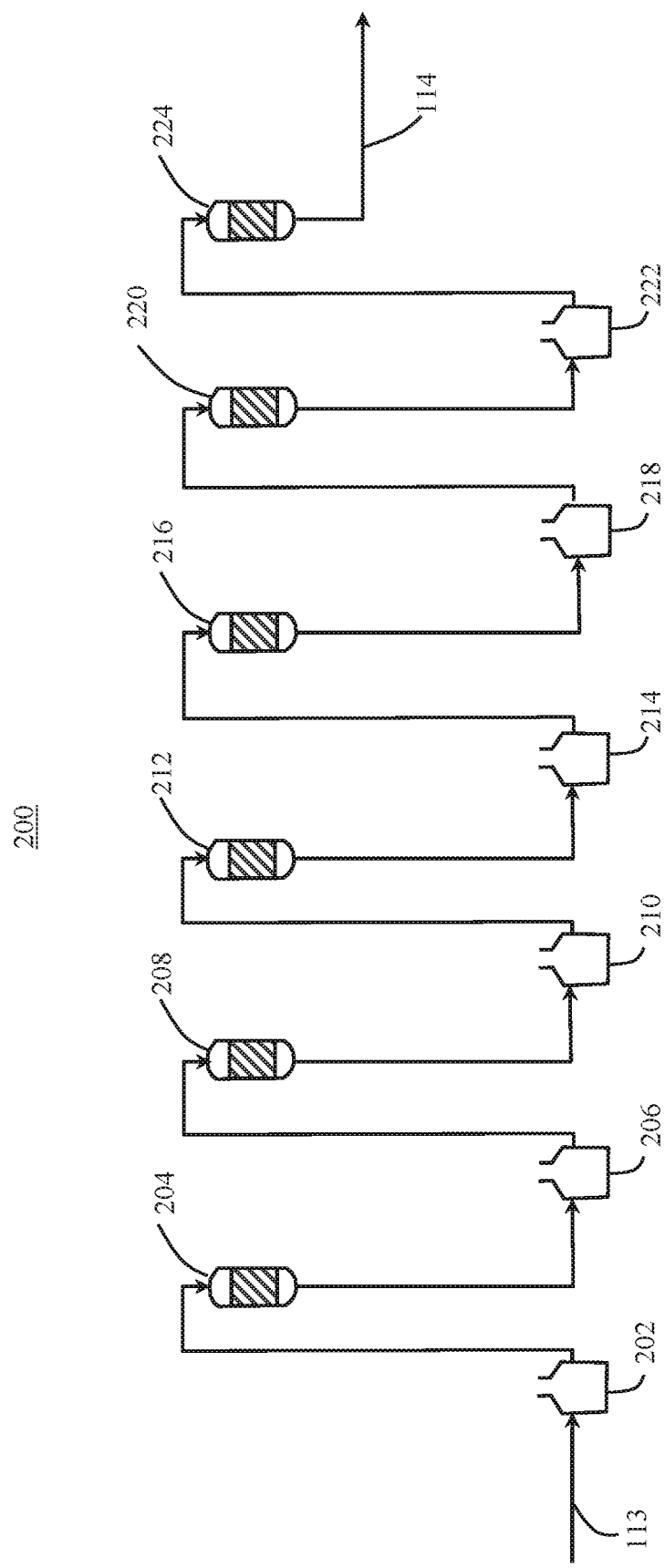
FIG. 7 illustrates a flow diagram of an aspect of a reactor section of the disclosure.

As shown in FIG. 7, the reforming reactor section 200 generally comprises a plurality of reactors 204, 208, 212, 216, 220, 224 arranged in series with furnaces 202, 206, 210, 214, 218, 222 located upstream of each reactor, respectively. In an embodiment, the combination of a furnace coupled to a downstream reactor may be referred to throughout the present specification as a "reactor-furnace pair." The furnaces 202, 206, 210, 214, 218, 222 may comprise any type of furnace capable of raising the temperature of the reactant stream to achieve the desired inlet temperature to the paired reactor. The temperature may be raised so that the reforming reactions proceed in the subsequent reactors, which is generally needed due to the endothermic nature of the reforming process.

The reactor section 200 may consist of a plurality of reactor-furnace pairs. In an embodiment, the reaction zone 200 comprises three or more serially connected reactors. All of the reactors 204, 208, 212, 216, 220, 224 can be the same or different in size or configuration. In an embodiment, all of the reactors 204, 208, 212, 216, 220, 224 are radial flow reactors with the hydrocarbon stream passing through the reactors in inward or outward flow. In an embodiment, the reactors may be sized according to known techniques, and all of the reactors may be the same size. Alternatively, one or more reactors may be different sizes.

As shown in FIG. 7, the hydrocarbon stream proceeds through the reactor train in a serial flow scheme. Between each reactor 204, 208, 212, 216, 220, 224, the hydrocarbon stream passes through a furnace 202, 206, 210, 214, 218, 222, respectively, to raise the temperature of the stream back to a desired reactor inlet temperature. Once heated, the stream is then returned to the next reactor until the reforming stream passes out of the final reactor in the series as the reforming effluent stream, which passes through line 114 to the downstream processing units.

Returning to FIG. 6, the reforming effluent stream passing through line 114 passes through both the second heat exchanger 110 and the first heat exchanger 106 to be cooled before passing to a trim cooler 116 for a final temperature adjustment before entering the separator 118. The separator 118 splits the reforming effluent stream into a liquid product stream 136 containing about 60 wt % to 90 wt % aromatics in the bottoms and a net-gas stream 128. This liquid product can be further purified to collect a higher percentage of aromatics in the stream, and any unreacted products can leave the process as another product stream or be recycled to the inlet of the process. The net-gas stream 128 from the top of separator 118 may pass through a compressor 120 and a cooler 122 before passing to separator 124. The separator 124 separates the compressed and cooled net-gas stream 128 into a hydrogen rich stream 130 from any remaining $C_5^+$ products. The remaining $C_5^+$ products are recycled to separator 118 through line 134. The hydrogen rich stream is split into a hydrogen product stream 131 and a recycle hydrogen stream 132. The recycle hydrogen stream 132 then passes through a drier 126 before passing through line 104 to re-enter the process along with the hydrocarbon stream passing through line 102. The hydrogen product stream 131 may be further purified to provide hydrogen for use in an industrial process (e.g., a refinery).

The hydrogen and methane mole data may be monitored by taking samples of the gaseous component stream at various locations within the system. Samples can be collected via any convenient piping or tubing in the catalytic reactor system 100: for example along the reactor effluent stream 114 before passing to separator 118, such as at the inlet or the outlet of second heat exchanger 110 or at the inlet or outlet of the first heat exchanger 106; or along the net-gas stream 128 before passing to separator 124, such as at the inlet or outlet of compressor 120 or at the inlet or outlet of cooler 122. In an aspect, samples can be collected from any gaseous component stream in between the effluent of the last reactor (e.g., reactor 224 of FIG. 7) and the junction where the recycle hydrogen stream passing through line 104 mixes with hydrocarbon stream passing through line 102 (i.e., any of streams 114, 118, 130, 132 and 104 of FIG. 6). Each sample may be analyzed with a gas analyzer such as a gas chromatograph. Commercially available gas-detector tubes or chip measurement systems, for example available by Gastec® or Drager, may be used.

In general, the reforming reaction occurs under process conditions that thermodynamically favor the dehydrocyclization reactions and limit undesirable hydrocracking reactions. The reforming reaction can be carried out using any conventional reforming conditions, and may be carried out at reactor inlet temperatures ranging from about 600° F. to about 1100° F., alternatively from about 650° F. to about 1100° F., alternatively from about 700° F. to about 1100° F., alternatively from about 800° F. to about 1050° F., alternatively from about 850° F. to about 1050° F. Reaction pressures may range from about atmospheric pressure to about 500 psig, alternatively from about 25 psig to about 300 psig, and alternatively from about 30 psig to about 100 psig. The molar ratio of hydrogen to hydrocarbon in the reactor stream is normally between about 0.1 and about 10, alternatively from about 0.5 to about 5.0, and alternatively from about 1:1 to about 3:1. The liquid hourly space velocity (LHSV) for the hydrocarbon feed over the aromatization catalyst is from about 0.5 to about 20, and alternatively from about 0.50 to about 5.0 based on the catalyst in the reaction zone.

In an embodiment, the reactors 204, 208, 212, 216, 220, 224 each contain a catalyst for carrying out a reforming process. As is known to those of ordinary skill in the art, a suitable reforming catalyst is capable of converting at least a portion of aliphatic, alicyclic, and/or naphthenic hydrocarbons (e.g., non-aromatic hydrocarbons) in a hydrocarbon stream to aromatic hydrocarbons. Any catalyst capable of carrying out a reforming reaction may be used alone or in combination with additional catalytic materials in the reactors. Suitable catalysts may include acidic or non-acidic catalysts. In an embodiment, the catalyst is a non-acidic catalyst. A suitable non-acidic catalyst may comprise a non-acidic zeolite support, at least one group VIII metal, and one or more halides. Suitable halides include chloride, fluoride, bromide, iodide, or combinations thereof. Suitable Group VIII metals include iron, cobalt, nickel, ruthenium, rhodium, palladium, osmium, iridium, platinum, or combinations thereof. Examples of catalysts suitable for use with the catalytic reactor system described herein are ARO-MAX® catalysts available from the Chevron Phillips Chemical Company LP of The Woodlands, Tex., and those discussed in U.S. Pat. No. 6,812,180 to Fukunaga entitled "Method for Preparing Catalyst" and U.S. Pat. No. 7,153,801 to Wu entitled "Aromatization Catalyst and Methods of Making and Using Same," each of which is incorporated herein by reference as if reproduced in their entirety.

The supports for catalysts can generally include any inorganic oxide. These inorganic oxides may include bound large pore aluminosilicates (zeolites), amorphous inorganic oxides and mixtures thereof. Large pore aluminosilicates can include, but are not limited to, L-zeolite, Y-zeolite, mordenite, omega zeolite, beta zeolite, and the like. Amorphous inorganic oxides can include, but are not limited to, aluminum oxide, silicon oxide, and titania. Suitable bonding agents for the inorganic oxides can include, but are not limited to, silica, alumina, clays, titania, and magnesium oxide.

Zeolite materials, both natural and synthetic, are known to have catalytic properties for many hydrocarbon processes. Zeolites typically are ordered porous crystalline aluminosilicates having structure with cavities and channels interconnected by channels. The cavities and channels throughout the crystalline material generally can be of a size to allow selective separation of hydrocarbons.

The term "zeolite" generally refers to a particular group of hydrated, crystalline metal aluminosilicates. These zeolites exhibit a network of $SiO_4$ and $AlO_4$ tetrahedra in which aluminum and silicon atoms are crosslinked in a three-dimensional framework by sharing oxygen atoms. In the framework, the ratio of oxygen atoms to the total of aluminum and silicon atoms may be equal to about 2. The framework exhibits a negative electrovalence that typically is balanced by the inclusion of cations within the crystal such as metals, alkali metals, alkaline earth metals, or hydrogen.

L-type zeolite catalysts are a sub-group of zeolitic catalysts. Typical L-type zeolites contain mole ratios of oxides in accordance with the following formula:

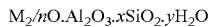

$$M_{2/n}O.Al_2O_3.xSiO_2.yH_2O$$

wherein "M" designates at least one exchangeable cation such as barium, calcium, cerium, lithium, magnesium, potassium, sodium, strontium, and zinc as well as non-metallic cations like hydronium and ammonium ions which may be replaced by other exchangeable cations without causing a substantial alteration of the basic crystal structure of the L-type zeolite. The "n" in the formula represents the valence of "M", "x" is 2 or greater; and "y" is the number of water molecules contained in the channels or interconnected voids with the zeolite. Bound potassium L-type zeolites, or KL zeolites, have been found to be particularly desirable. The term "KL zeolite" as used herein refers to L-type zeolites in which the principal cation M incorporated in the zeolite is potassium. A KL zeolite may be cation-exchanged or impregnated with another metal and one or more halides to produce a platinum-impregnated, halided zeolite or a KL supported Pt-halide zeolite catalyst.

In an embodiment, the at least one Group VIII metal is platinum. In another embodiment, the at least one Group VIII metal is platinum and gold. In an embodiment, the at least one Group VIII metal is platinum and rhenium. The platinum and optionally one or more halides may be added to the zeolite support by any suitable method, for example via impregnation with a solution of a platinum-containing compound and one or more halide-containing compounds. For example, the platinum-containing compound can be any decomposable platinum-containing compound. Examples of such compounds include, but are not limited to, ammonium tetrachloroplatinate, chloroplatinic acid, diammineplatinum (II) nitrite, bis-(ethylenediamine)platinum (II) chloride, platinum (II) acetylacetonate, dichlorodiammine platinum, platinum (II) chloride, tetraammineplatinum (II) hydroxide, tetraammineplatinum chloride, and tetraammineplatinum (II) nitrate.

In an embodiment, the catalyst is a large pore zeolite support with a platinum-containing compound and at least one ammonium halide compound. The ammonium halide compound may comprise one or more compounds represented by the formula $N(R)_4X$, where X is a halide and where R represents a hydrogen or a substituted or unsubstituted carbon chain molecule having 1-20 carbons wherein each R may be the same or different. In an embodiment, R is selected from the group consisting of methyl, ethyl, propyl, butyl, and combinations thereof, more specifically methyl. Examples of suitable ammonium compounds are represented by the formula $N(R)_4X$ include ammonium chloride, ammonium fluoride, and tetraalkylammonium halides such as tetramethylammonium chloride, tetramethylammonium fluoride, tetraethylammonium chloride, tetraethylammonium fluoride, tetrapropylammonium chloride, tetrapropylammonium fluoride, tetrabutylammonium chloride, tetrabutylammonium fluoride, methyltriethylammonium chloride, methyltriethylammonium fluoride, and combinations thereof.

The catalyst can be employed in any of the conventional types or structures known to the art. It may be employed in the form of extrudates, pills, pellets, granules, broken fragments, or various special shapes, disposed within a reaction zone (e.g., in a fixed bed), and the charging stock may be passed there through in the liquid, vapor, or mixed phase, and in either upward or downward, or inward or outward flow.

In an aspect, a reforming process is operated while monitoring a $H_2/CH_4$ mole ratio until the $H_2/CH_4$ mole ratio indicates that a reforming catalyst may be deemed to have reached an EOR stage (i.e., the reforming catalyst has become spent). In a further aspect, while operating the reforming process at least one reactor may experience a decrease in catalytic performance (e.g., activity or selectivity) over time. The resulting deactivation of the catalyst can result from a number of mechanisms including, but not limited to, coking, poisoning, and/or loss of catalytic material or components. As used herein, the term "coke" refers to a carbon-rich carbonaceous material, generally having a C/H ratio>1. The term "coking" refers to the process of depositing coke on a surface. Both the term "coke" and "coking" as used herein are meant to include the conventional meaning known in the art. In an aspect, a catalyst can be deemed a spent catalyst when the catalytic activity is less than or equal to about 50%, alternatively about 40%, alternatively about 30%, alternatively 20%, or alternatively 10% of the initial catalytic activity of the catalyst when initially placed into service. In an embodiment, a catalyst can be deemed a spent catalyst when the catalytic selectivity as measured by methane production is more than or equal to about 150% of the catalyst when initially placed into service. In an embodiment, a catalyst may be deemed to be a spent catalyst based on catalyst performance, alone or in combination with operational considerations, and/or economic considerations. For example, the catalyst may be deemed to be spent when the income attributable to improved conversion efficiency, and thus increased product yield, as a result of replacing the catalyst outweighs the expense of replacing the catalyst.

In an aspect a reforming process comprises a plurality of reactors that are used to carry out a reforming reaction until a catalyst in at least one of the reactors is deemed to be spent. In another aspect the reforming process comprises a single reactor that is used to carry out the reforming reaction until the catalyst in the single reactor is deemed to be spent. The ability of the at least one reactor containing the spent catalyst to convert aliphatic, alicyclic, and/or naphthenic hydrocarbons in the hydrocarbon stream to aromatic hydrocarbons may then be restored. In an embodiment, the ability to convert aliphatic, alicyclic, and/or naphthenic hydrocarbons to aromatic hydrocarbons may be restored by replacing the spent catalyst in the at least one reactor with fresh catalyst, regenerating the catalyst, and/or rejuvenating the catalyst. Regeneration and rejuvenation are described in more detail below. Suitable procedures known in the art may be used to replace the spent catalyst in the at least one reactor with fresh catalyst at desired intervals. In an embodiment, each reactor may be restored at an equal time interval based on the expected life of the catalyst in the reforming process which may be determined via the methods of monitoring catalytic performance as described herein. In an embodiment, each reactor may be restored based on measurable indicators of the catalyst activity as determined via the methods of monitoring catalytic performance as described herein. Additional indicators of the need for corrective action optionally may be monitored as well. For example, an outlet temperature rise may indicate a loss of activity for an endothermic reaction, and/or a decrease in the product concentration at the outlet of the reactor may indicate a decrease in the catalyst activity or performance. The fresh catalyst has a higher activity or performance as compared to the spent catalyst. The spent catalyst may then be disposed of or recycled to recover the active catalytic materials for future use. The catalyst can be regenerated in accordance with any known regeneration procedure for sulfur sensitive catalysts as described in more detail below.

Regeneration generally refers to restoring the catalyst by removing one or more contaminants on the catalyst. For example, regeneration may involve the conversion of carbonaceous material on the catalyst to carbon oxides and water. Decoking is one example of a regeneration process. In this process, oxygen, which may be supplied in the form of air, is provided to the at least one reactor (e.g., an isolated reactor for in-situ regeneration) at an appropriate temperature. The carbon deposits are thereby oxidized to form carbon dioxide and water. The water is subsequently removed from the system.

In an embodiment, a regeneration process may be carried out by heating the spent catalyst to a temperature ranging of from about 25° C. to about 1000° C., alternatively from about 50° C. to about 900° C., alternatively from about 100° C. to about 800° C., alternatively from 200° C. to 700° C., alternatively from 300° C. to 600° C. to produce a decoked spent catalyst. The decoking process may be carried out by heating the spent catalyst for a time of from about 1 hour to about 40 hours, alternatively from about 2 hours to about 25 hours, alternatively from about 3 hours to about 20 hours, alternatively from 4 hours to 15 hours, alternatively from 5 hours to 10 hours to produce a decoked spent catalyst. As discussed above, the decoking process may be carried out by heating the spent catalyst in the presence of oxygen, and the oxygen concentration may be from about 0.01 mol % to about 20 mol % alternatively from about 0.1 mol % to about 15 mol % alternatively from about 0.2 mol % to about 10 mol % alternatively from 0.5 mol % to 5 mol % alternatively from 1 mol % to 3 mol % to produce a decoked spent catalyst. Suitable regeneration processes that can be used in accordance with the present invention are disclosed in U.S. Pat. No. 4,937,215 to Murakawa et al., U.S. Pat. No. 5,260,238 to Murakawa et al., U.S. Pat. No. 5,155,075 to Innes et al., U.S. Pat. No. 4,851,380 to Van Leirsburg et al., and U.S. Pat. No. 7,868,217 to Brown et al., each of which is incorporated herein by reference as if reproduced in their entirety.

As used herein, rejuvenation refers to a process of reactivating a spent catalyst by decreasing coke content, redispersing metals, and/or introducing a replacement and/or additional catalytic component to the catalyst in order to increase the activity of the catalyst. In an embodiment, rejuvenating the spent catalyst comprises redispersing the metal in the spent catalyst to produce a redispersed spent catalyst, contacting the redispersed spent catalyst with a reactivating composition to produce a redispersed, reactivated spent catalyst, and thermally treating the redispersed, reactivated spent catalyst to produce a reactivated catalyst. Optionally rejuvenation can be preceded by a regeneration procedure.

In an embodiment, rejuvenating the spent catalyst may begin by decoking the catalyst. Any of the decoking processes described above with respect to the regeneration of the spent catalyst may be used to decoke the catalyst. Following decoking of the spent catalyst, the metal on the decoked spent catalyst may be redispersed on the catalyst support. While not wishing to be bound by theory, the decoking process in combination with the hydrocarbon conversion process that the spent catalyst was subjected to, may have led to the agglomeration of the metal on the catalyst support. The agglomerated metal may not be fully available physically and chemically to the catalytic reactions and thus may be redispersed to increase the catalyst activity.

In an embodiment, the metal on the decoked spent catalyst is redispersed using one or more processes generally referred to as oxychlorination. Oxychlorination of the decoked spent catalyst may be carried out by contacting the decoked spent catalyst with a redispersing composition. Suitable redispersing compositions may comprise a chorine-containing compound and oxygen. The chlorine-containing compound may be in the solid phase, liquid phase, gas phase, or any combination thereof. Examples of chlorine-containing compounds suitable for use in the redispersing composition include without limitation hydrochloric acid, chlorine, carbon tetrachloride, tetrachloroethylene, chlorobenzene, methyl chloride, methylene chloride, chloroform, allyl chloride, trichloroethylene, chloramine, chlorine oxides, chlorine acids, chlorine dioxide, dichlorine monoxide, dichlorine heptoxide, chloric acid, perchloric acid, or any combination thereof.

Contacting of the decoked, spent catalyst with the redispersing composition may be carried out over a time period of from about 0.5 hours to about 50 hours, alternatively from about 1 hour to about 20 hours, alternatively from about 2 hours to about 10 hours, at a temperature in the range of from about 25° C. to about 1000° C., alternatively from about 50° C. to about 900° C., alternatively from about 100° C. to about 800° C., alternatively from about 200° C. to about 400° C., alternatively from about 400° C. to about 600° C. Contacting of the decoked, spent catalyst with the redispersing composition may be carried out in the presence of oxygen. When oxygen is used the oxygen concentration may range from about 0.01 mol % to about 20 mol %, alternatively from about 1 mol % to about 18 mol %, alternatively from about 5 mol % to about 15 mol %, alternatively from about 8 mol % to about 12 mol %.

In an embodiment, the decoked, spent catalyst is contacted with a redispersing composition comprising a chorine-containing compound (e.g., HCl) and oxygen in the presence of water. When water is used, the water to HCl mole ratio ($H_2O:HCl$) may be from about 0.01:1 to about 10:1, alternatively from about 0.5:1 to about 5:1, alternatively from about 1:1 to about 3:1. When chorine-containing compounds are used other than HCl, the $H_2O:HCl$ mole ratio is calculated based on the equivalent amount of HCl generated in the presence of the spent catalyst.

A spent catalyst may be subjected to a reactivation step, which may occur after the decoked spent catalyst has undergone a redispered as described above. In an embodiment, reactivation of the decoked, redispersed spent catalyst may be carried out using a reactivating composition comprising one or more halogenating agents, including gas phase halogenating agents, liquid phase halogenating agents, solid phase halogenating agents, or any combination thereof. In an embodiment, reactivation of the decoked, redispersed spent catalyst is carried out by contacting the decoked, redispersed spent catalyst with a fluorine-containing solution in a process generally referred to as fluoridation. The fluorine-containing compound may be in the solid phase, liquid phase, gas phase, or any combination thereof. Examples of fluorine-containing compounds suitable for use in this disclosure include without limitation tetramethylammonium fluoride (TMAF), ammonium fluoride ($NH_4F$ or AF), tetrafluoroethylene, 2,2,2-trifluoroethanol (TFE), fluorine ($F_2$), hydrofluoric acid (HF), or combinations thereof. In an embodiment, the fluorine-containing compound is a perfluorinated alkane, perfluornated alcohol or mixtures thereof. Examples of perfluorinated alcohols suitable for use in this disclosure include without limitation 2,2,2-trifluoroethanol (TFE), hexafluoroisopropanol, tetrafluoropropanol, pentafluoropropanol, hexafluorophenylpropanol, perfluorobutyl alcohol, hexafluor-2-propanol, pentafluoro-1-propanol, tetrafluoro-1-propanol, 1,1,1,3,3,3-hexafluoro-2-propanol, 2,2,3,3,3-pentafluoro-1-propanol, and any combination thereof.

In an embodiment, the fluorine-containing compound is an ammonium halide compound and may comprise one or more compounds represented by the general formula $N(R)_4F$, where R represents a hydrogen or a substituted or unsubstituted carbon chain molecule having from 1 to 20 carbons wherein each R may be the same or different. In an embodiment, R is methyl, ethyl, propyl, butyl, or combinations thereof. Alternatively, R is methyl. Examples of suitable ammonium compounds include ammonium fluoride (AF), tetramethylammonium fluoride (TMAF), tetraethylammonium fluoride (TEAF), tetrapropylammonium fluoride, tetrabutylammonium fluoride, methyltriethylammonium fluoride, or any combination thereof. Alternatively, the ammonium halide compound may also comprise at least one hydrofluoric acid and at least one ammonium hydroxide represented by the formula $N(R')_4OH$, where R' is hydrogen or a substituted or unsubstituted carbon chain molecule having from 1 to 20 carbon atoms wherein each R' may be the same or different. In an embodiment, R' is methyl, ethyl, propyl, butyl, or combinations thereof. Alternatively, R' is methyl. Examples of ammonium hydroxides suitable for use in this disclosure include ammonium hydroxide, tetraalkylammonium hydroxides such as tetramethylammonium hydroxide, tetraethylammonium hydroxide, tetrapropylammonium hydroxide, tetrabutylammonium hydroxide, or any combination thereof.

In an embodiment the decoked, redispersed spent catalyst is contacted with a solution of TMAF in the temperature range of from about 0° C. to about 200° C., alternatively from about 20° C. to about 100° C., alternatively from about 40° C. to about 60° C. for a time period of from about 1 minute to about 100 hours, alternatively about 0.1 hours to about 50 hours, alternatively from about 1 hour to about 24 hours. The solution may also contain one or more suitable solvents.

In an embodiment, the decoked, redispersed spent catalyst may be reactivated through contact with a gas phase fluoridating agent such as, for example, fluorine. In such an embodiment, the gas phase fluoridating agent may be contacted with a decoked, redispersed spent catalyst for a time period of from about 1 minute to about 100 hours, alternatively from about 0.1 hours to about 50 hours, alternatively from about 1 hour to about 24 hours, alternatively from about 4 hours to about 11 hours.

In an embodiment, the decoked, redispersed spent catalyst may be reactivated through contact with a solid phase fluoridating agent such as an organic ammonium halide compound, for example ammonium fluoride, tetramethylammonium fluoride, or any combination thereof. In such an embodiment, the solid phase fluoridating agent may be contacted with a decoked, redispersed spent catalyst at elevated temperatures. The contacting may occur for a time period of from about 1 minute to about 100 hours, alternatively from about 0.1 hours to about 50 hours, alternatively from about 1 hour to about 24 hours, alternatively from about 4 hours to about 11 hours. The elevated temperatures may in the temperature range of from about 0° C. to about 200° C., alternatively from about 20° C. to about 100° C., alternatively from about 40° C. to about 60° C. While not wishing to be limited by theory it is believed that under these conditions some of the solid phase fluoridating agent sublimes and migrates into the decoked, redispersed spent catalyst.

A chorine-containing compound may also be utilized in the reactivation of the decoked, redispersed spent catalyst. The chlorine-containing compound may be in the solid phase, liquid phase, gas phase, or any combination thereof. In an embodiment, the chlorine-containing compound is of the type described above. Examples of chlorine-containing compounds suitable for use in the reactivating composition include without limitation compounds represented by the general formula $NR_4Cl$, where R represents a hydrogen or a substituted or unsubstituted carbon chain molecule having 1 to 20 carbons wherein each R may be the same or different. In an embodiment, R is methyl, ethyl, propyl, butyl, or combinations thereof. Alternatively R is methyl. Specific examples of suitable organic ammonium chlorine compounds include ammonium chloride, tetramethylammonium chloride (TMAC), tetraethylammonium chloride, tetrapropylammonium chloride, tetrabutylammonium chloride, methyltriethylammonium chloride, or combinations thereof. Alternatively, the chorine-containing compound is TMAC.

In addition to the embodiments disclosed herein for regenerating and/or rejuvenating the catalyst, suitable processes for regenerating and/or rejuvenating the catalyst are described in U.S. Pat. No. Re. 34,250 to Van Leirsburg et al., U.S. Pat. No. 4,810,683 to Cohn et al., U.S. Pat. No. 5,776,849 to Fung et al., U.S. Pat. No. 4,855,269 to Mohr, U.S. Pat. No. 4,925,819 to Fung et al., U.S. Pat. No. 5,106,798 to Fung, and U.S. Patent Application Publication No. 2010-0160147 to Wu, each of which is incorporated herein by reference in its entirety. European patent disclosure 316,727, which is also hereby incorporated by reference in its entirety, also describes a process for rejuvenating deactivated Pt-L-zeolite catalysts by treating the catalyst at about 930° F. with a halogen compound such as carbon tetrachloride and nitrogen. Oxygen is then added to the mixture to remove coke and, finally, the catalyst is treated with a chlorofluorocarbon compound, oxygen, and nitrogen.

Also disclosed herein is a computer system comprising one or more processors; a non-transitory memory coupled to the processor, wherein the non-transitory memory comprises executable instructions that, when executed, cause the one or more processors to: obtain a first set of data from the reforming process for each of a plurality of values for each of a CAF, a $H_2/CH_4$ mole ratio, and a DOS; model a catalytic performance of the reforming catalyst with a catalytic performance model to determine two or more first best-fit curves; calculate values for a mole ratio end-of-run (M-EOR) and a DOS end-of-run (D-EOR); obtain a second set of data from the reforming process for values for a current $H_2/CH_4$ mole ratio and a current DOS; compare the current $H_2/CH_4$ mole ratio to the M-OER and the current DOS to the D-EOR; and signal that the reforming catalyst may be deemed to have reached an end-of-run condition. In an embodiment, the computer system may communicate with or form a part of a computerized control system of a reforming reactor system as described in more detail herein.

Figure 8:
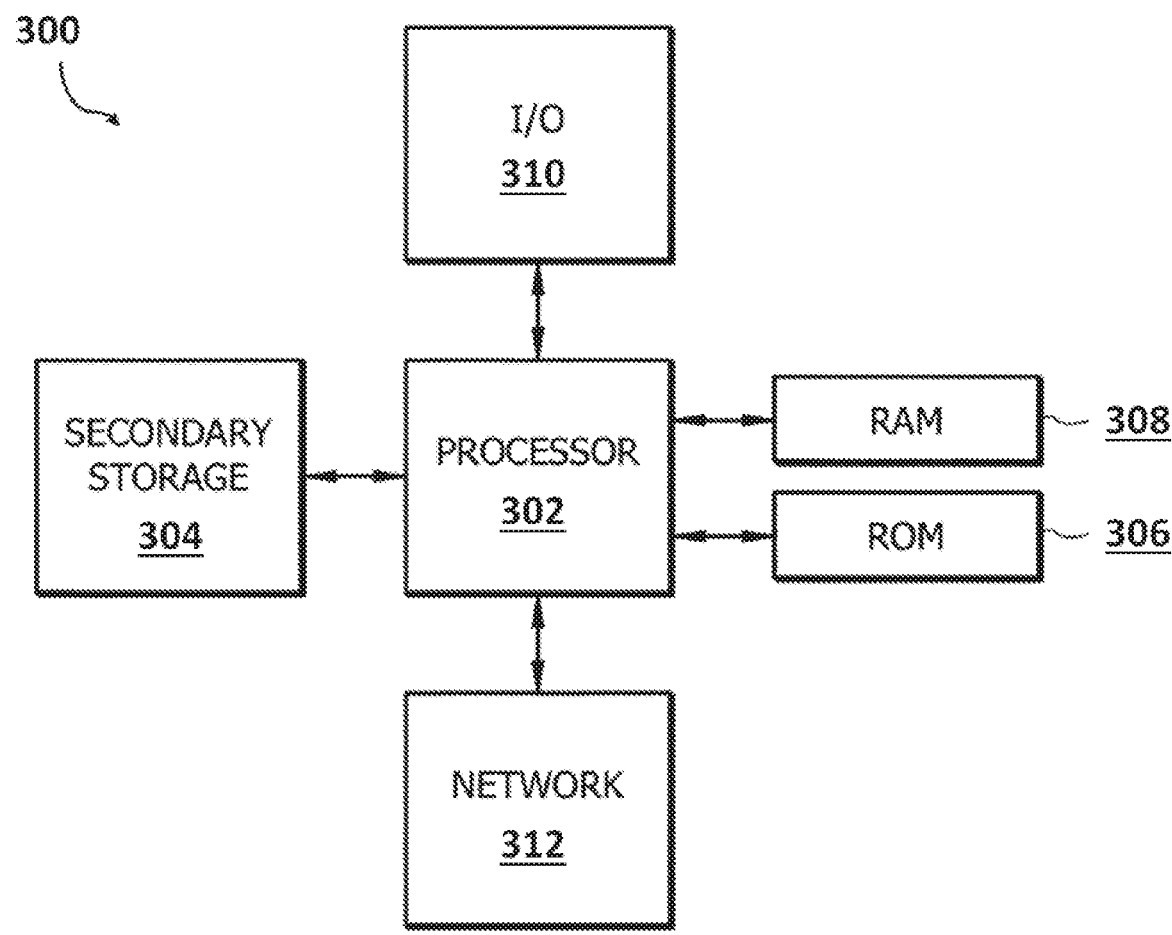
FIG. 8 illustrates a computer system suitable for implementing one or more aspects of the disclosure.

FIG. 8 illustrates a computer system 300 suitable for implementing all, or a portion of, one or more embodiments disclosed herein. All of, or a portion of, the system 300 may be implemented on any particular machine, or machines, with sufficient processing power, memory resources, and throughput capability to handle the necessary workload placed upon the computer, or computers. The computer system 300 includes a processor 302 (which may be referred to as a central processor unit or CPU) that is in communication with memory devices including secondary storage 304, read only memory (ROM) 306, random access memory (RAM) 308, input/output (I/O) devices 310, and network connectivity devices 312. The processor 302 may be implemented as one or more CPU chips.

It is understood that by programming and/or loading executable instructions onto the computer system 300, at least one of the CPU 302, the RAM 308, and the ROM 306 are changed, transforming the computer system 300 in part into a particular machine or apparatus having the novel functionality taught by the present disclosure. It is fundamental to the electrical engineering and software engineering arts that functionality that can be implemented by loading executable software into a computer can be converted to a hardware implementation by well-known design rules. Decisions between implementing a concept in software versus hardware typically hinge on considerations of stability of the design and numbers of units to be produced rather than any issues involved in translating from the software domain to the hardware domain. Generally, a design that is still subject to frequent change may be preferred to be implemented in software, because re-spinning a hardware implementation is more expensive than re-spinning a software design. Generally, a design that is stable that will be produced in large volume may be preferred to be implemented in hardware, for example in an application specific integrated circuit (ASIC), because for large production runs the hardware implementation may be less expensive than the software implementation. Often a design may be developed and tested in a software form and later transformed, by well-known design rules, to an equivalent hardware implementation in an application specific integrated circuit that hardwires the instructions of the software. In the same manner as a machine controlled by a new ASIC is a particular machine or apparatus, likewise a computer that has been programmed and/or loaded with executable instructions may be viewed as a particular machine or apparatus.

The secondary storage 304 is typically comprised of one or more disk drives or tape drives and is used for non-volatile storage of data and as an over-flow data storage device if RAM 308 is not large enough to hold all working data. Secondary storage 304 may be used to store programs which are loaded into RAM 308 when such programs are selected for execution. The ROM 306 is used to store instructions and perhaps data which are read during program execution. ROM 306 is a non-volatile memory device which typically has a small memory capacity relative to the larger memory capacity of secondary storage 304. The RAM 308 is used to store volatile data and perhaps to store instructions. Access to both ROM 306 and RAM 308 is typically faster than to secondary storage 304. The secondary storage 304, the RAM 308, and/or the ROM 306 may be referred to in some contexts as computer readable storage media and/or non-transitory computer readable media.

I/O devices 310 may include printers, video monitors, liquid crystal displays (LCDs), touch screen displays, keyboards, keypads, switches, dials, mice, track balls, voice recognizers, card readers, paper tape readers, or other well-known input devices.

The network connectivity devices 312 may take the form of modems, modem banks, Ethernet cards, universal serial bus (USB) interface cards, serial interfaces, token ring cards, fiber distributed data interface (FDDI) cards, wireless local area network (WLAN) cards, radio transceiver cards such as code division multiple access (CDMA), global system for mobile communications (GSM), long-term evolution (LTE), worldwide interoperability for microwave access (WiMAX), and/or other air interface protocol radio transceiver cards, and other well-known network devices. These network connectivity devices 312 may enable the processor 302 to communicate with the Internet or one or more intranets. With such a network connection, it is contemplated that the processor 302 might receive information from the network, or might output information to the network in the course of performing the above-described method steps. Such information, which is often represented as a sequence of instructions to be executed using processor 302, may be received from and outputted to the network, for example, in the form of a computer data signal embodied in a carrier wave.

Such information, which may include data or instructions to be executed using processor 302 for example, may be received from and outputted to the network, for example, in the form of a computer data baseband signal or signal embodied in a carrier wave. The baseband signal or signal embedded in the carrier wave, or other types of signals currently used or hereafter developed, may be generated according to several methods well known to one skilled in the art. The baseband signal and/or signal embedded in the carrier wave may be referred to in some contexts as a transitory signal.

The processor 302 executes instructions, codes, computer programs, scripts which it accesses from hard disk, floppy disk, optical disk (these various disk based systems may all be considered secondary storage 304, ROM 306, RAM 308, or the network connectivity devices 312. While only one processor 302 is shown, multiple processors may be present. Thus, while instructions may be discussed as executed by a processor, the instructions may be executed simultaneously, serially, or otherwise executed by one or multiple processors. Instructions, codes, computer programs, scripts, and/or data that may be accessed from the secondary storage 304, for example, hard drives, floppy disks, optical disks, and/or other device, the ROM 306, and/or the RAM 308 may be referred to in some contexts as non-transitory instructions and/or non-transitory information.

In an embodiment, the computer system 300 may comprise two or more computers in communication with each other that collaborate to perform a task. For example, but not by way of limitation, an application may be partitioned in such a way as to permit concurrent and/or parallel processing of the instructions of the application. Alternatively, the data processed by the application may be partitioned in such a way as to permit concurrent and/or parallel processing of different portions of a data set by the two or more computers. In an embodiment, virtualization software may be employed by the computer system 300 to provide the functionality of a number of servers that is not directly bound to the number of computers in the computer system 300. For example, virtualization software may provide twenty virtual servers on four physical computers. In an embodiment, the functionality disclosed above may be provided by executing the application and/or applications in a cloud computing environment. Cloud computing may comprise providing computing services via a network connection using dynamically scalable computing resources. Cloud computing may be supported, at least in part, by virtualization software. A cloud computing environment may be established by an enterprise and/or may be hired on an as-needed basis from a third party provider. Some cloud computing environments may comprise cloud computing resources owned and operated by the enterprise as well as cloud computing resources hired and/or leased from a third party provider.

In an embodiment, some or all of the functionality disclosed above may be provided as a computer program product. The computer program product may comprise one or more computer readable storage medium having computer usable program code embodied therein to implement the functionality disclosed above. The computer program product may comprise data structures, executable instructions, and other computer usable program code. The computer program product may be embodied in removable computer storage media and/or non-removable computer storage media. The removable computer readable storage medium may comprise, without limitation, a paper tape, a magnetic tape, magnetic disk, an optical disk, a solid state memory chip, for example analog magnetic tape, compact disk read only memory (CD-ROM) disks, floppy disks, jump drives, digital cards, multimedia cards, and others. The computer program product may be suitable for loading, by the computer system 300, at least portions of the contents of the computer program product to the secondary storage 304, to the ROM 306, to the RAM 308, and/or to other non-volatile memory and volatile memory of the computer system 300. The processor 302 may process the executable instructions and/or data structures in part by directly accessing the computer program product, for example by reading from a CD-ROM disk inserted into a disk drive peripheral of the computer system 300. Alternatively, the processor 302 may process the executable instructions and/or data structures by remotely accessing the computer program product, for example by downloading the executable instructions and/or data structures from a remote server through the network connectivity devices 312. The computer program product may comprise instructions that promote the loading and/or copying of data, data structures, files, and/or executable instructions to the secondary storage 304, to the ROM 306, to the RAM 308, and/or to other non-volatile memory and volatile memory of the computer system 300.

In some contexts, the secondary storage 304, the ROM 306, and the RAM 308 may be referred to as a non-transitory computer readable medium or a computer readable storage media. A dynamic RAM embodiment of the RAM 308, likewise, may be referred to as a non-transitory computer readable medium in that while the dynamic RAM receives electrical power and is operated in accordance with its design, for example during a period of time during which the computer 300 is turned on and operational, the dynamic RAM stores information that is written to it. Similarly, the processor 302 may comprise an internal RAM, an internal ROM, a cache memory, and/or other internal non-transitory storage blocks, sections, or components that may be referred to in some contexts as non-transitory computer readable media or computer readable storage media.

In an embodiment, the computer system 300 (through, e.g., the network connectivity devices 312) is capable of facilitating communications between the processor 302 and components of the catalytic reactor system 100 of FIG. 6. In an embodiment, the network connectivity devices 312 may be wired devices such as Ethernet cards, USB interface cards, etc., or combinations thereof, and the communications between the processor 302 and the components of the catalytic reactor system 100 may be wired network communications. Alternatively, the network connectivity devices 312 may be wireless devices such as WiFi, Bluetooth, etc. and the communications between the processor 302 and the components of the catalytic reactor system 100 may be wireless network communications.

In an embodiment, components of the catalytic reactor system 100 may be coupled to the computer system 300 such that data obtained from one or more components may be stored and/or used by the computer system 300. In an embodiment, the mole ratio end-of-run (M-EOR) and a DOS end-of-run (D-EOR) may be calculated as a function of the CAF, a $H_2/CH_4$ mole ratio, and a DOS using the computer system 300. After calculating, the M-EOR and may be selected by a user of the computer system 300 or by the computer system 300 itself (e.g., under system or user-defined guidelines), for example. The computer system 300 may communicate with one or more components of the catalytic reactor system 100 so as to set or adjust operating parameters to maximize the D-EOR.

ADDITIONAL DISCLOSURE

The following are non-limiting, specific aspects in accordance with the present disclosure:

A first aspect which is a method of monitoring catalytic performance of a catalyst used in a reforming process, comprising: a. collecting gaseous component data from the reforming process; b. calculating a gaseous component ratio from the gaseous component data; and c. utilizing the gaseous component ratio to estimate an amount of catalytic activity remaining in the catalyst used in the reforming process, a number of days on stream remaining for the catalyst used in the reforming process, or both.

A second aspect which is the method of the first aspect wherein the gaseous component data comprises moles of hydrogen and moles of methane and wherein the gaseous component ratio comprises a ratio of moles of hydrogen to moles of methane.

A third aspect which is the method of any of the first through second aspects wherein collecting gaseous component data from the reforming process further comprises collecting a gas sample from a gaseous component stream of the reforming process and subjecting the gas sample to gas chromatography.

A fourth aspect which is the method of any of the first through third aspects wherein step c further comprises utilizing a correlation of baseline data for the ratio of moles of hydrogen to moles of methane and catalyst activity, a correlation of baseline data for the ratio of moles of hydrogen to moles of methane and days on stream, or both.

A fifth aspect which is a method of modeling catalytic performance of a catalyst used in a reforming process, comprising: a. constructing a two-coordinate graph containing a vertical axis for gaseous component ratio data and a horizontal axis for catalyst activity factor data; b. obtaining a set of gaseous component ratio data and a set of catalyst activity factor data for the reforming process; c. representing the set of gaseous component ratio data and the set of catalyst activity factor data upon the two-coordinate graph; and d. constructing a best-fit curve upon the two-coordinate graph, wherein the best-fit curve represents a graphical relationship of the set of gaseous component ratio data and the set of catalyst activity factor data.

A sixth aspect which is the method of the fifth aspect, further comprising: e. assigning a catalyst activity end-of-run value and representing the catalyst activity end-of-run value as a vertical line upon the two-coordinate graph; and f. determining a point of intersection of the best-fit curve with the vertical line and assigning a vertical axis value of the point of intersection as a gaseous component ratio end-of-run value.

A seventh aspect which is the method of any of the fifth through sixth aspects wherein the gaseous component ratio data comprises a ratio of moles of hydrogen to moles of methane wherein the gaseous component ratio end-of-run value comprises a mole ratio end-of-nm (M-EOR) value and wherein the gaseous component ratio data is obtained via gas chromatography.

An eighth aspect which is the method of any of the fifth through seventh aspects wherein the best-fit curve is constructed from gaseous component ratio data and catalyst activity factor data obtained from an ongoing reforming process, an equation or historical reforming process data.

A ninth aspect which is the method of any of the fifth through eighth aspects wherein the graphical relationship of the best-fit curve is about linear and wherein the graphical relationship remains about linear during the reforming process.

A tenth aspect which is method of modeling catalytic performance of a catalyst used in a reforming process, comprising: a. constructing a two-coordinate graph containing a vertical axis for gaseous component ratio data and a horizontal axis for days-on-stream (DOS) data; b. obtaining a set of gaseous component ratio data and a set of DOS data or the reforming process; c. representing the set of gaseous component ratio data and the set of DOS data upon the two-coordinate graph; and d. constructing a best-fit curve upon the two-coordinate graph, wherein the best-fit curve represents a graphical relationship of the set of gaseous component ratio data and the set of DOS data.

An eleventh aspect which is the method of the tenth aspect further comprising: e. assigning a gaseous component ratio end-of-run value and representing the gaseous component ratio end-of-run value as a horizontal line upon the two-coordinate graph; and f. determining a point of intersection of the best-fit curve with the horizontal line and assigning a horizontal axis value of the point of intersection as a DOS end-of-run (D-EOR) value.

A twelfth aspect which is the method of any of the tenth through eleventh aspects wherein the gaseous component ratio data comprises a ratio of moles of hydrogen to moles of methane wherein the gaseous component ratio end-of-run value comprises a mole ratio end-of-nm (M-EOR) value and wherein the gaseous component ratio data is obtained via gas chromatography.

A thirteenth aspect which is the method of any of the tenth through twelfth aspects wherein the best-fit curve is constructed from gaseous component ratio data and DOS data obtained from an ongoing reforming process, an equation, or historical reforming process data.

A fourteenth aspect which is the method of any of the tenth through thirteenth aspects wherein the graphical relationship of the best-fit curve is about linear and wherein the graphical relationship remains about linear during the reforming process.

A fifteenth aspect which is a method of monitoring the catalytic performance of a catalyst used in a reforming process, comprising: a. collecting a gas sample from a gaseous component stream of the reforming process; b. determining a ratio of moles of hydrogen to moles of methane in the gas sample; c. comparing the ratio of moles of hydrogen to moles of methane in the gas sample to a M-EOR value; and d. signaling that the reforming catalyst may be deemed to have reached an end-of-run condition when the ratio of moles of hydrogen to moles of methane in the gas sample is within a threshold range relative to the M-EOR value.

A sixteenth aspect which is the method of the fifteenth aspect wherein the threshold range is from about 95% to about 105% of to the M-EOR value.

A seventeenth aspect which is the method of any of the fifteenth through sixteenth aspects further comprising initiating a corrective action upon the reforming catalyst.

An eighteenth aspect which is the method of any of the fifteenth through seventeenth aspects wherein the corrective action comprises halting operation of the reforming process, replacing all or a portion of the reforming catalyst, regenerating all or a portion of the reforming catalyst, or combinations thereof.

A nineteenth aspect which is a model prepared by the method of the fifth aspect, wherein the model is a mathematical function representing the best-fit curve.

A twentieth aspect which is a method of monitoring the catalytic performance of a catalyst used in a reforming process, comprising: a. inputting a catalyst activity end-of-run value into the model of the nineteenth aspect and determining a corresponding mole ratio end-of-run (M-EOR) value; b. collecting a gas sample from a gaseous component stream of the reforming process; c. determining a ratio of moles of hydrogen to moles of methane in the gas sample; d. comparing the ratio of moles of hydrogen to moles of methane in the gas sample to the M-EOR value; and e. signaling that the reforming catalyst may be deemed to have reached an end-of-run condition when the ratio of moles of hydrogen to moles of methane in the gas sample is within a threshold range relative to the M-EOR value.

A twenty-first aspect which is a model prepared by the method of the tenth aspect wherein the model is a mathematical function representing the best-fit curve.

A twenty-second aspect which is a method of monitoring the catalytic performance of a catalyst used in a reforming process, comprising: a. inputting a mole ratio end-of-run (M-EOR) value into the model of the twenty-first aspect and determining a corresponding DOS end-of-run (D-EOR) value; b. comparing the current DOS data to the D-EOR value; and c. signaling that the reforming catalyst may be deemed to have reached an end-of-run condition when the current DOS data is within a threshold range relative to the D-EOR value.

A twenty-third aspect which is a method for catalytic reforming comprising: a. providing a hydrocarbon feed stream to one or more reactors; b. contacting the hydrocarbon feed stream with a reforming catalyst in the one or more reactors; c. obtaining a first set of data from the reforming process for each of a plurality of values for each of a CAF, a $H_2/CH_4$ mole ratio, and a DOS; d. modeling a catalytic performance of the reforming catalyst with a catalytic performance model to determine a first best-fit curve based on the plurality of values for each of the CAF and the $H_2/CH_4$ mole ratio, and a second best-fit curve based on the plurality of values for each of the $H_2/CH_4$ mole ratio and the DOS; e. calculating a value for a mole ratio end-of-run (M-EOR) from a value of a catalyst activity factor end-of-run (C-EOR) using the first best-fit curve and a value for a DOS end-of-run (D-EOR) from M-EOR using the second best-fit curve; f. operating the one or more reactors and obtaining a second set of data from the reforming process for values for each of a current $H_2/CH_4$ mole ratio and a current DOS; g. comparing the current $H_2/CH_4$ mole ratio to the M-OER and the current DOS to the D-EOR; and h. signaling that the reforming catalyst may be deemed to have reached an end-of-run condition when the current $H_2/CH_4$ mole ratio is within a threshold range relative to the M-EOR or when the current DOS is within a threshold range relative to the D-EOR.

A twenty-fourth aspect which is a method for catalytic reforming comprising: a. providing a hydrocarbon feed stream to one or more reactors and contacting the hydrocarbon feed stream with a reforming catalyst in the one or more reactors; b. modeling catalytic performance of the reforming catalyst with a catalytic performance model by; i. obtaining data from the reforming process for each of a plurality of values for each of a gaseous component ratio, a catalyst activity factor (CAF), and a days on stream (DOS); ii. determining a first best-fit curve based on the plurality of values for each of the gaseous component ratio and the CAF data using a first two coordinate system; iii. determining a second best-fit curve based on the plurality of values for each of the gaseous component ratio and the DOS data using a second two coordinate system; iv. assigning a value for a catalyst activity factor end-of-run (C-EOR); v. calculating a value for a mole ratio end-of-run (M-EOR) from a value of the catalyst activity factor end-of-run (C-EOR) using the first best-fit curve and a value for a DOS end-of-run (D-EOR) from the M-EOR using the second best-fit curve; c. collecting a gas sample from a gaseous component stream of the reforming process; d. calculating a gaseous component ratio in the gas sample; e. comparing the gaseous component ratio in the gas sample to the M-OER and a current DOS to the D-EOR; and f. signaling that the reforming catalyst may be deemed to have reached an end-of-nm condition when the gaseous component ratio in the gas sample is within a threshold range relative to the M-EOR or when the current DOS is within a threshold range relative to the D-EOR.

A twenty-fifth aspect which is the method of the twenty-fourth aspect wherein the gaseous component ratio comprises a ratio of moles of hydrogen to moles of methane.

A twenty-sixth aspect which is the method of any of the twenty-fourth through twenty-fifth aspects wherein obtaining the gaseous component ratio further comprises collecting a gas sample from a gaseous component stream of the reforming process.

A twenty-seventh aspect which is the method of any of the twenty-fourth through twenty-sixth aspects wherein one or more gas samples are subjected to gas chromatography.

A twenty-eighth aspect which is the method of any of the twenty-fourth through twenty-seventh aspects wherein the first best-fit curve is determined by using data obtained from an ongoing reforming process, an equation or an historical reforming process data and the second best fit curve best fit is determined by using data obtained from an ongoing reforming process, an equation or an historical reforming process.

A twenty-ninth aspect which is the method of any of the twenty-fourth through twenty-eighth aspects wherein the first best-fit curve is about linear and remains about linear during the reforming process and wherein the second best-fit curve is about linear and remains about linear during the reforming process.

A thirtieth aspect which is the method of any of the twenty-fourth through twenty-ninth aspects wherein calculating a value for the M-EOR further comprises determining an equality or intersection of the C-EOR value with the first best fit curve and wherein calculating a value for the D-EOR further comprises determining a equality or intersection of the M-EOR with the second best fit curve.

A thirty-first aspect which is the method of any of the twenty-fourth through thirtieth aspects wherein the signaling in step f occurs when gaseous component ratio in the gas sample is from about 95% to about 105% of the M-EOR or when the current DOS is from about 95% to about 105% of the D-EOR.

A thirty-second aspect which is the method of any of the twenty-fourth through thirty-first aspects wherein the signaling in step f further comprises initiating a corrective action upon the reforming catalyst.

A thirty-third aspect which is the method of the thirty-second aspect wherein the corrective action comprises halting operation of the reforming process, replacing all or a portion of the reforming catalyst, regenerating all or a portion of the reforming catalyst, rejuvenating all or a portion of the reforming catalyst, or combinations thereof.

While the present disclosure has been illustrated and described in terms of particular apparatus and methods of use, it is apparent that equivalent techniques, components and constituents may be substituted for those shown, and other changes can be made within the scope of the present disclosure as defined by the appended claims.

The particular embodiments disclosed herein are illustrative only, as the disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope and spirit of the disclosure. Accordingly, the protection sought herein is as set forth in the claims below.

We claim:

1. A method of modeling catalytic performance of a catalyst used in a reforming process, comprising:
   a. constructing a two-coordinate graph containing a vertical axis for gaseous component ratio data and a horizontal axis for catalyst activity factor data;
   b. obtaining a set of gaseous component ratio data and a set of catalyst activity factor data for the reforming process;
   c. representing the set of gaseous component ratio data and the set of catalyst activity factor data upon the two-coordinate graph;
   d. constructing a best-fit curve upon the two-coordinate graph, wherein the best-fit curve represents a graphical relationship of the set of gaseous component ratio data and the set of catalyst activity factor data;
   e. assigning a catalyst activity end-of-run value and representing the catalyst activity end-of-run value as a vertical line upon the two-coordinate graph; and
   f. determining a point of intersection of the best-fit curve with the vertical line and assigning a vertical axis value of the point of intersection as a gaseous component mole ratio end-of-run (M-EOR) value.

2. A model prepared by the method of claim 1, wherein the model is a mathematical function representing the best-fit curve.

3. The method of claim 1 wherein the gaseous component ratio data comprises a ratio of moles of hydrogen to moles of methane and wherein the gaseous component ratio data is obtained via gas chromatography.

4. The method of claim 3 wherein the best-fit curve is constructed from gaseous component ratio data and catalyst activity factor data obtained from an ongoing reforming process, an equation, or historical reforming process data.

5. The method of claim 4 wherein the graphical relationship of the best-fit curve is about linear and wherein the graphical relationship remains about linear during the reforming process.

6. A method of modeling catalytic performance of a catalyst used in a reforming process, comprising:
   a. constructing a two-coordinate graph containing a vertical axis for gaseous component ratio data and a horizontal axis for days-on-stream (DOS) data;
   b. obtaining a set of gaseous component ratio data and a set of DOS data for the reforming process;
   c. representing the set of gaseous component ratio data and the set of DOS data upon the two-coordinate graph; and
   d. constructing a best-fit curve upon the two-coordinate graph, wherein the best-fit curve represents a graphical relationship of the set of gaseous component ratio data and the set of DOS data;
   e. assigning a gaseous component ratio end-of-run value and representing the gaseous component ratio end-of-run value as a horizontal line upon the two-coordinate graph; and
   f. determining a point of intersection of the best-fit curve with the horizontal line and assigning a horizontal axis value of the point of intersection as a DOS end-of-run (D-EOR) value.

7. A model prepared by the method of claim 6, wherein the model is a mathematical function representing the best-fit curve.

8. The method of claim 6 wherein the gaseous component ratio data comprises a ratio of moles of hydrogen to moles of methane wherein the gaseous component ratio end-of-run value comprises a mole ratio end-of-run (M-EOR) value and wherein the gaseous component ratio data is obtained via gas chromatography.

9. The method of claim 8 wherein the best-fit curve is constructed from gaseous component ratio data and DOS data obtained from an ongoing reforming process, an equation, or historical reforming process data.

10. The method of claim 9 wherein the graphical relationship of the best-fit curve is about linear and wherein the graphical relationship remains about linear during the reforming process.

* * * * *